(12) United States Patent
Reed et al.

(10) Patent No.: US 7,202,272 B2
(45) Date of Patent: Apr. 10, 2007

(54) COMPOUND

(75) Inventors: Michael John Reed, London (GB); Barry Victor Lloyd Potter, Bath (GB)

(73) Assignee: Sterix, Ltd., Berkshire (GB)

( * ) Notice: Subject to any disclaimer, the term of this patent is extended or adjusted under 35 U.S.C. 154(b) by 0 days.

(21) Appl. No.: 10/991,137

(22) Filed: Nov. 17, 2004

(65) Prior Publication Data

US 2005/0154050 A1 Jul. 14, 2005

Related U.S. Application Data

(60) Division of application No. 09/638,314, filed on Aug. 14, 2000, now Pat. No. 6,921,776, which is a continuation-in-part of application No. 09/238,345, filed on Jan. 27, 1999, now Pat. No. 6,187,766, which is a division of application No. 09/111,927, filed on Jul. 8, 1998, now Pat. No. 6,011,024, which is a continuation-in-part of application No. PCT/GB97/00444, filed on Feb. 17, 1997, which is a continuation-in-part of application No. 09/125,255, filed as application No. PCT/GB97/00444 on Feb. 17, 1997, now Pat. No. 6,239,169.

(30) Foreign Application Priority Data

Feb. 16, 1996 (GB) ................................. 9603325.3

(51) Int. Cl.
*A61K 31/352* (2006.01)
(52) U.S. Cl. ..................................................... 514/455
(58) Field of Classification Search ................. 514/455
See application file for complete search history.

(56) References Cited

U.S. PATENT DOCUMENTS

| 4,600,788 A | 7/1986 | Creuzet et al. |
| 4,618,622 A | 10/1986 | Schlecker et al. |
| 4,829,084 A | 5/1989 | Bailey |
| 6,011,024 A | 1/2000 | Reed et al. |
| 6,239,169 B1 | 5/2001 | Reed et al. |

FOREIGN PATENT DOCUMENTS

| AU | 645975 | 12/1990 |
| EP | 0 111 746 | 11/1983 |
| EP | 0 403 185 | 6/1990 |
| FR | 2543140 | 3/1983 |
| WO | WO 92/21353 | 12/1992 |
| WO | WO 93/05064 | 3/1993 |
| WO | WO 97/32872 | 9/1997 |

OTHER PUBLICATIONS

Ballabio, A. et al., "Steroid Sulfatase Deficiency and X-Linked Ichthyosis," Part 18: Hormones, Chapter 166: 4241-4262, 2001.

Corral, C. et al., "Synthesis and Anticholinesterase Activity of a Series of Aryl N,N-dimethylsulfamates," *Chemical Abstracts*, 62: 7070, 1965.
Hernandez-Martin, A. et al., "X-linked Ichthyosis: an Update," *British J. Derm.*, 141: 617-627, 1999.
Howarth, N. et al., "Estrone Sulfamates: Potent Inhibitors of Estrone Sulfatase with Therapeutic Potential," *J. Med. Chem.*, 37: 219-221, 1994.
Nelson, K. et al., "Murine Arylsulfatase C: Evidence for Two Isozymes," *Experientia*, 39: 740-42, 1983.
Purohit, A. et al., "Inactivation of Steroid Sulfatase by an Active Site-Directed Inhibitor, Estrone-3-O-Sulfamate," *Biochemistry*, 34: 11508-11514, 1995.
Reed, M.J. et al., "The Role of Cytokines and Sulphatase Inhibitors in Regulating Oestrogen Synthesis in Breast Tumours," *J. Steroid Biochem. Molec. Biol.*, 53(1-6): 413-420, 1995.
Sahm, U.G. et al., "Development of an Oral Formulation for Oestrone 3-O-Sulphamate, a Potent Sulphatase Inhibitor," *Pharmaceutical Sciences*, 2: 17-20, 1996.
Woo, L.W. et al., "Active Site Directed Inhibition of Estrone Sulfatase by Nonsteroidal Coumarin Sulfamates," *J. Med. Chem.*, 39: 1349-51, 1996.
Woo, L.W. et al., "Heteroatom-Substituted Analogues of the Active-Site Directed Inhibitor Estra-1,3,5(10)-Trien-17-One-3-Sulphamate Inhibit Estrone Sulphatase by a Different Mechanism," *J. Steroid Biochem. Molec. Biol.*, 57(1/2): 79-88, 1996.
Corral and Municio, "Sintesis Y Actividad Anticolesterasica de una serie de N, N-Dimetilsulfamatos de Arilo," *Anales de Fisica Y Quimica* 1964; 60 (4): 341-344.

*Primary Examiner*—Taofiq Solola
(74) *Attorney, Agent, or Firm*—Frommer Lawrence & Haug LLP; Thomas J. Kowalski; Angela M. Collison

(57) ABSTRACT

A compound is described. In particular, a non-steroidal sulphamate compound is described. The compound is suitable for use as an inhibitor of oestrone sulphatase. The compound is of general Formula (A),

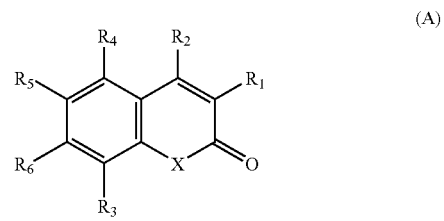

(A)

wherein $R_1$–$R_6$ are independently selected from H, halo, hydroxy, sulphamate, alkyl and substituted variants or salts thereof; but wherein at least one of $R_1$–$R_6$ is a sulphamate group; and wherein X is any one of S, NH, a substituted N, $CH_2$, or a substituted C.

8 Claims, 12 Drawing Sheets

(A)

(B)

(C)

(D)

(E)

(F)

(G)

(H)

COMPOUND

RELATED APPLICATIONS

This application is a division of allowed U.S. application Ser. No. 09/638,314, filed Aug. 14, 2000 now U.S. Pat. No. 6,921,776, which is a continuation-in-part of allowed U.S. application Ser. No. 09/238,345, filed Jan. 27, 1999 now U.S. Pat. No. 6,187,776, which was a division of U.S. application Ser. No. 09/111,927, filed Jul. 8, 1998, now U.S. Pat. No. 6,011,024, which in turn was a continuation-in-part of inter alia PCT patent application No. PCT/GB97/00444, filed Feb. 17, 1997, designating the U.S., and claiming priority from United Kingdom patent application 9603325.3, filed Feb. 16, 1996. PCT/GB97/00444 was published as WO 97/30041 on Aug. 21, 1997. This application is also a continuation-in-part of allowed U.S. application Ser. No. 09/125,255, filed Aug. 14, 1998 now U.S. Pat. No. 6,239,169 as the National Phase (35 USC 371) of PCT/GB97/00444, Feb. 17, 1997, designating the U.S., published as WO 97/30041 on Aug. 21, 1997, and claiming priority from United Kingdom patent application 9603325.3, filed Feb. 16, 1996. Each of these applications and patents and each document cited or referenced in each of these applications and patents, including during any prosecution ("application cited documents"), and each document cited or referenced in each of the application cited documents, are hereby incorporated herein by reference. In addition, each document cited in this text ("herein cited documents") and each document cited or referenced in each of the herein cited documents, are hereby incorporated herein by reference.

The present invention relates to a compound.

In particular the present invention relates to a non-steroidal compound and to a pharmaceutical composition comprising the non-steroidal compound.

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours[1,2]. This theory is supported by a modest reduction of plasma oestrogen concentration in postmenopausal women with breast cancer treated by aromatase inhibitors, such as aminoglutethimide and 4-hydroxyandrostenedione[3,4] and also by the fact that plasma E1S concentration in these aromatase inhibitor-treated patients remains relatively high. The long half-life of E1S in blood (10–12 h) compared with the unconjugated oestrogens (20 min)[5] and high levels of steroid sulphatase activity in liver and, normal and malignant breast tissues, also lend support to this theory[6].

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE").

EMATE is a potent E1-STS inhibitor as it displays more than 99% inhibition of E1-STS activity in intact MCF-7 cells at 0.1 μM. EMATE also inhibits the E1-STS enzyme in a time- and concentration-dependent manner, indicating that it acts as an active site-directed inactivator[7,8]. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol[8,9]. Also, there is now evidence to suggest that androstenediol may be of even greater importance as a promotor of breast tumour growth[10]. EMATE is also active in vivo as almost complete inhibition of rat liver E1-STS (99%) and DHA-STS (99%) activities resulted when it is administered either orally or subcutaneously[11]. In addition, EMATE has been shown to have a memory enhancing effect in rats[14]. Studies in mice have suggested an association between DHA-STS activity and the regulation of part of the immune response. It is thought that this may also occur in humans[15,16]. The bridging O-atom of the sulphamate moiety in EMATE is important for inhibitory activity. Thus, when the 3-O-atom is replaced by other heteroatoms (FIG. 1) as in oestrone-3-N-sulphamate (4) and oestrone-3-S-sulphamate (5), these analogues are weaker non-time-dependent inactivators[12].

Although optimal potency for inhibition of E1-STS may have been attained in EMATE, it is possible that oestrone may be released during sulphatase inhibition[8,12], and that EMATE and its oestradiol congener may possess oestrogenic activity[13].

The present invention therefore seeks to provide compounds suitable for the inhibition of E1-STS but which have no, or a minimal, oestrogenic effect.

According to a first aspect of the present invention there is provided a non-steroidal sulphamate compound suitable for use as an inhibitor of oestrone sulphatase, wherein the compound has a polycyclic ring structure comprising at least a first ring and a second ring; wherein the first ring and the second ring mimic the A and B rings of oestrone; and wherein the polycyclic ring structure is not tetrahydronaphthol.

Preferably either the first ring or the second ring comprises an α,β-unsaturated lactone group.

Preferably the first ring is a phenolic ring.

Preferably the compound has a bicyclic ring structure.

Preferably the compound has the general Formula (A) (see FIG. 8). In Formula (A) $R_1$–$R_6$ are independently selected from H, halo, hydroxy, sulphamate, alkyl and substituted variants or salts thereof; but wherein at least one of $R_1$–$R_6$ is a sulphamate group; and wherein X is any one of O, S, NH, a substituted N, $CH_2$, or a substituted C.

Preferably X is O.

Preferably, if the sulphamate group of the compound were to be replaced with a sulphate group to form a sulphate compound then that sulphate compound would be hydrolysable by an enzyme having steroid sulphatase (E.C. 3.1.6.2) activity.

In a highly preferred embodiment, the compound is not hydrolysable by an enzyme having steroid sulphatase (E.C. 3.1.6.2) activity.

According to a second aspect of the present invention there is provided a non-steroidal compound wherein the compound has the general Formula (B) (see FIG. 8). In Formula (B) $R_1-R_6$ are independently selected from H, halo, hydroxy, sulphamate, alkyl and substituted variants or salts thereof; but wherein at least one of $R_1-R_6$ is a sulphamate group.

According to a third aspect of the present invention there is provided the compound 4-methyl coumarin-7-0-sulphamate.

According to a fourth aspect of the present invention there is provided a non-steroidal compound according to the present invention for use as a pharmaceutical.

According to a fifth aspect of the present invention there is provided a non-steroidal compound according to the present invention for inhibiting oestrone sulphatase According to a sixth aspect of the present invention there is provided a pharmaceutical composition comprising a non-steroidal compound according to the present invention; and a pharmaceutically acceptable carrier, excipient or diluent.

According to a seventh aspect of the present invention there is provided the use of a non-steroidal compound according to the present invention in the manufacture of a pharmaceutical for inhibiting oestrone sulphatase.

According to an eighth aspect of the present invention there is provided a process for preparing a compound according to the present invention, the process comprising sulphating a coumarin.

According to a ninth aspect of the present invention there is provided a process for preparing a compound according to the present invention, the process comprising sulphamaylating a coumarin.

The alkyl group(s) in Formula (A) or Formula (B) can be any suitable linear or branched alkyl group which may be saturated or unsaturated and/or substituted or non-substituted. The alkyl group may even be a cyclic alkyl group. For example, at least two of $R_{1-6}$ are linked to form a further cyclic component.

Preferably $R_1-R_5$ are independently selected from H, alkyl and haloalkyl; preferably wherein $R_1-R_5$ are independently selected from H, C1–6 alkyl and C1–6 haloalkyl.

Preferably $R_1-R_5$ are independently selected from H, C1–3 alkyl and C1–3 haloalkyl.

Preferably $R_1-R_5$ are independently selected from H, methyl and halomethyl.

Preferably $R_6$ is $OSO_2NH_2$.

Preferably the compound is any one of the compounds shown as Compounds 12–16 in FIG. 2.

Preferably the compound is 4-methyl coumarin-7-0-sulphamate.

In Formula (A) or Formula (B), two or more of $R_1-R_6$ may be linked together to form an additional cyclic structure. A typical example of such a compound has the general Formula (C) (see FIG. 8), wherein any one of $R_3-R_6$ is a sulphamate group, and wherein n is an integer. Typically, $R_6$ is a sulphamate group. A typical sulphamate group is —OS(O)(O)—$NH_2$. Preferably n is an integer of from 3 to 10, preferably from 3 to 7. Optionally, the group $(CH_2)_n$ of Formula (C) can be a substituted alkyl chain.

Typical compounds falling within the general Formula (C) are shown in FIG. 9 as compound (D) (where n=3), compound (E) (where n=4), compound (F) (where n=5), compound (G) (where n=6), compound (H) (where n=7). For these compounds, $R_6$ is a sulphamate group of the formula —OS(O)(O)—$NH_2$ and each of $R_3-R_5$ is H.

The term "sulphamate" as used herein includes an ester of sulphamic acid, or an ester of an N-substituted derivative of sulphamic acid, or a salt thereof. Thus, the term includes functional groups of the formula: —O—S(O)(O)—N($R_7$)($R_8$) where $R_7$ and $R_8$ are independently selected from H, halo, linear or branched alkyl which may be saturated or unsaturated and/or substituted or non-substituted, aryl, or any other suitable group. Preferably, at least one or $R_7$ and $R_8$ is H. In a preferred embodiment, each of $R_7$ and $R_8$ is H.

The term "mimic" as used herein is used in its normal sense—namely having a different structure but having a similar functional effect.

A key advantage of the non-steroidal compound of the present invention is that it is potent in vivo and that it has less oestrogenic activity and can therefore be deemed to be a "non-oestrogenic compound". The term "non-oestrogenic compound" as used herein means a compound exhibiting no or substantially no oestrogenic activity.

The present invention therefore provides non-steroidal compounds which have a reduced oestrogenic activity. In this regard, the non-steroidal compounds of the present invention act as E1-STS inhibitors.

Another advantage is that the compounds may not be capable of being metabolised to compounds which display or induce hormonal activity.

The compounds of the present invention are also advantageous in that they are orally active.

The compounds of the present invention are further advantageous in that they may have an irreversible effect.

The compounds of the present invention are further advantageous in that they may also inhibit DHA-STS.

Thus, in a preferred embodiment, the non-steroidal compounds are useful for the treatment of breast cancer. In addition, the non-steroidal compounds are useful for the treatment of non-malignant conditions, such as the prevention of auto-immune diseases, particularly when pharmaceuticals may need to be administered from an early age.

A particularly preferred non-steroidal compound according to the present invention is 4-methyl coumarin-7-O-sulphamate. This compound is particularly advantageous in that it acts as a time- and a concentration-dependent inhibitor in a similar manner to EMATE. Another key advantage of this non-steroidal compound is that it is an orally active irreversible compound. In addition, it is not metabolised to compounds with hormonal activity.

A highly preferred embodiment of the present invention therefore relates to a pharmaceutical composition comprising 4-methyl coumarin-7-O-sulphamate and a pharmaceutically acceptable carrier, excipient or diluent.

The present invention therefore relates to non-steroidal compounds which are suitable for use as sulphatase inhibitors.

In addition to being potent in vivo sulphatase inhibitors, the compounds of the present invention have reduced, or even minimal or no, oestrogenic activity.

Studies have shown that the sulphamates of the present invention inhibit enzyme E1-ETS in intact MCF-7 cells in a dose dependent manner with similar potencies to EMATE.

Of the preferred coumarin sulphamates, 4-methylcoumarin-7-O-sulphamate together with coumarin-7-O-sulphamate appear particularly active in vitro. In this regard, 4-methylcoumarin-7-O-sulphamate inhibited E1-STS by 93.3% at 10 μM with an $IC_{50}$ of 380 nM in intact MCF-7 breast cancer cells. This inactivation was shown to be time- and concentration-dependent inhibitor in a similar way to EMATE. 4-methylcoumarin-7-O-sulphamate also inhibited placental microsomal dehydro-epiandrosterone sulphatase by 93.6% at 10 μM. This compound also shows a reduced oestrogenic activity as was seen by the lack of significant increase in the uterine weight in treated ovariectomised rats.

The compound also has a potent oral activity.

The non-steroidal compounds of the present invention, in particular the preferred coumarin sulphamates, represent important compounds for the optimisation of non-steroidal sulphatase inhibition. The compounds are also believed to have therapeutic uses other than for the treatment of endocrine-dependent cancers, such as the treatment of autoimmune diseases.

BRIEF DESCRIPTION OF THE DRAWINGS

The present invention will now be described only by way of example with reference to the accompanying drawings in which.

EXAMPLES

The compounds of the present invention may be prepared by a process that comprises a Pechmann synthesis step. Pechmann synthesis is known in the art.

Sulphamoylation of Coumarins

Figure 4:
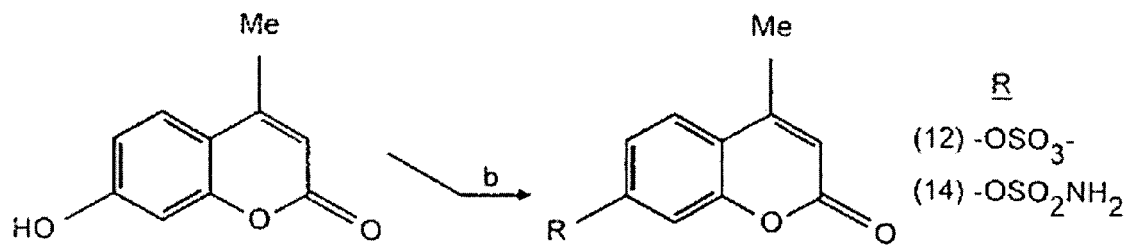
FIG. 4 shows the sulphamoylation of 7-hydroxy-4-methylcoumarin; NaH/DMF, $H_2NSO_2Cl$ in toluene (Route b)

The general procedure for the sulphamoylation of coumarins was as follows. A solution of an appropriate coumarin in anhydrous DMF (ca. 40 ml per g of coumarin) was treated with sodium hydride [60% dispersion; 1 equiv] at 0° C. under an atmosphere of $N_2$. After evolution of hydrogen had ceased, sulphamoyl chloride in toluene [ca. 0.68 M, 1.5 equiv] was added and the reaction mixture was poured into water after warming to room temperature overnight and then the crude product was then quenched. The organic fraction in ethyl acetate (150 ml) was washed exhaustively with brine, dried ($MgSO_4$), filtered and evaporated. The crude product obtained was purified by flash chromatography followed by recrystallisation to give the corresponding sulphamate. All new compounds were fully characterised by spectroscopic and combustion analysis. The synthesis of 4 methylcoumarin-7-O-sulphamate (14) is shown in FIG. 4.

Figure 1:
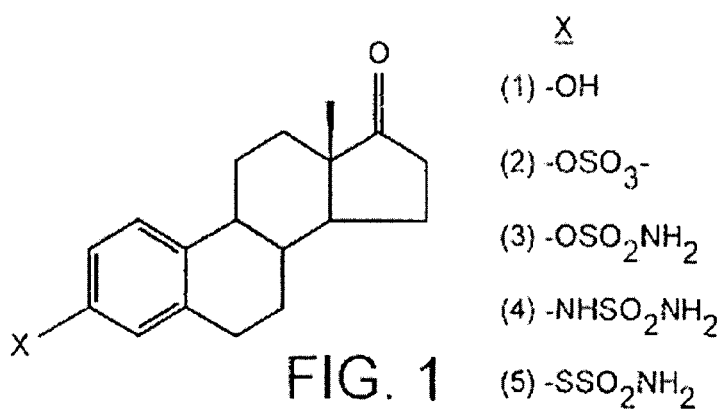
FIG. 1 shows the known structures of oestrone (1), oestrone sulphate (2), EMATE (3) and steroid sulphamates (4–5)
Figure 2:
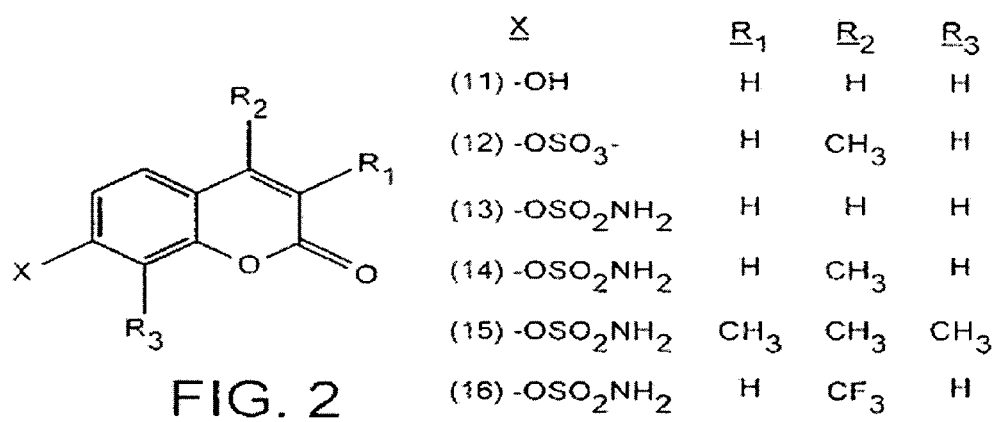
FIG. 2 shows the structures of 7-hydroxycoumarin (11), 7-(sulphoxy)-4-methylcoumarin (12) and coumarin sulphamates (13–16)

Following this general procedure, compounds 13–16 (as shown in FIG. 2)—i.e. coumarin-7-O-sulphamate (13), 4-methylcoumarin-7-O-sulphamate (14), 3,4,8-trimethyl-coumarin-7-O-sulphamate (15) and 4-(trifluoromethylcoumarin)-7-O-sulphamate (16)—were prepared. More details on the synthesis of these compounds now follow.

The synthesis of compound 12 (as shown in FIG. 2) is also discussed below.

Preparation of Coumarin-7-O-sulphamate (13)

Following the above-mentioned general procedure, 7-Hydroxycoumarin (500 mg, 3.082 mmol) gave a crude product (605 mg) which was fractionated on silica (200 g) by gradient elution with chloroform/acetone (8:1, 500 ml; 4:1, 1000 ml and then 2:1, 500 ml). Upon evaporation, the second fraction gave a creamy yellow residue (389 mg, 52.3%) which was recrystallised in ethyl acetate/hexane (1:1) to give (13) as dull white crystals (239 mg).

Analytical data were as follows:

M.p. 170.0–171.5° C.; $R_f$s=0.48 (ether), 0.67 (ethyl acetate), 0.19 (chloroform/acetone, 4:1); vmax (KBr) 3360, 3210, 3060, 1720, 1615, 1370, 1125 cm$^{-1}$; $\delta_H$ (DMSO-d$_6$/CDCl$_3$, ca. 1:25) 6.415 (1H, d, $J_{C-4-H, C-3-H}$=9.7 Hz, C-3-$\underline{H}$), 7.285 (1H, dd, $J_{C-8-H, C-6-H}$=2.3 Hz and $J_{C-5-H, C-6-H}$=8.5 Hz, C-6-H), 7.379 (1H, d, $J_{C-6-H,\ C-8-H}$=2.2 Hz, C-8-H), 7.508 (2H, br s, D$_2$O exchanged, —NH$_2$), 7.543 (1H, d, $J_{C-6-H,\ C-5-H}$=8.4 Hz, C-5-H) and 7.760 (1H, d, $J_{C-3-H,\ C-4-H}$=9.7 Hz, C-4-H). MS: m/z (E.I., rel. intensity) 241.0(10), 162.0(97), 134.0(100), 105.0(23). Acc. MS: m/z 241.0068, C$_9$H$_7$NO$_5$S requires 241.0045. Found: C, 44.8; H, 2.89; N, 5.82. C$_9$H$_7$NO$_5$S requires C, 44.81; H, 2.92; N, 5.81%.

Preparation of 4-Methylcoumarin-7-O-sulphamate (14)

Following the above-mentioned general procedure, 7-Hydroxy-4-methylcoumarin (500 mg, 2.753 mmol) gave a crude product (633 mg) which was fractionated on silica (200 g) by gradient elution with chloroform/acetone (8:1, 500 ml; 4:1, 1000 ml, 2:1, 500 ml and then 1:1, 500 ml). Upon evaporation, the second fraction gave a creamy yellow residue (425 mg, 60.5%) which was recrystallised in acetone/chloroform (3:5) to give (14) as colorless rhombic crystals (281 mg).

Analytical data were as follows:

M.p. 165–167° C.; R$_f$s=0.48 (ether), 0.29 (ether/hexane 8:1), 0.26 (chloroform/acetone, 4:1); vmax (KBr) 3320, 3180, 3080, 1700, 1620, 1560, 1380, 1125 cm$^{-1}$; $\delta_H$ (acetone-d$_6$) 2.507 (3H, s, —CH$_3$), 6.339 (1H, s, C-3-H), 7.299 (2H, m, C-6-H and C-8-H), 7.390 (2H, br s, D$_2$O exchanged, —NH$_2$) and 7.850 (1H, d, $J_{C-6-H,\ C-5-H}$=9 Hz, C-5-H). MS: m/z (+ve ion FAB in m-NBA, rel. intensity) 542.2(15), 511.1[45, (2M+H)$^+$], 461.2(20), 409.1[60, (M+H+NBA)$^+$], 393.3[60, (M+H+NBA-16)$^+$], 329.2[10, (M+H+NBA-80)$^+$], 256.1 [100, (M+H)$^+$]. MS: m/z (–ve ion FAB in m-NBA, rel. intensity) 421.0(20), 407.1[15, (M–H+NBA)], 335.1(14), 254[100, (M–H)$^-$], 175.1[32, (M–H-79)$^-$], 121.0(17). Found: C, 47.2; H, 3.56; N, 5.51. C$_{10}$H$_9$NO$_5$S requires C, 47.06; H, 3.55; N, 5.49%.

Preparation of 3,4,8-Trimethylcoumarin-7-O-sulphamate (15)

Following the above-mentioned general procedure, 7-Hydroxy-3,4,8-trimethylcoumarin (1.0 g, 4.896 mmol) gave a crude product (1.33 g) which upon recrystallisation in hot ethyl acetate yielded 238 mg of starting coumarin. The mother liquor was evaporated and the white residue obtained (1.13 g) was fractionated on silica (200 g) with ether. The second fraction was collected, evaporated and the residue obtained (519 mg, 37.4%) was recrystallised in acetone/hexane (1:2) to give (15) as pale yellow crystals (312 mg).

Analytical data were as follows:

M.p. 197–202° C.; R$_f$s=0.50 (ether), 0.69 (ethyl acetate); vmax (KBr) 3310, 3040, 1680, 1600 cm$^{-1}$; $\delta_H$ (acetone-d$_6$) 2.176, 2.383 and 2.458 (9H, three s, 3×CH$_3$), 1.374 (1H, d, $J_{C-5-H,\ C-6-H}$=8.8 Hz, C-6-H), 7.390 (2H, br s, D$_2$O exchanged, —NH$_2$) and 7.682 (1H, d, $J_{C-6-H,\ C-5-H}$=8.8 Hz, C-5-H). MS: m/z (E.I., rel. intensity) 283.1(10), 204.1(45), 176.1(40), 161.1(22), 69.1(56), 57.1(40), 43.1(100). Acc. MS: m/z 283.0497, C$_{12}$H$_{13}$NO$_5$S requires 283.0514. Found: C, 50.86; H, 4.63; N, 4.97. C$_{12}$H$_{13}$NO$_5$S requires C, 50.88; H, 4.63; N, 4.94%.

Preparation of 4-(Trifluoromethyl)coumarin-7-O-sulphamate (16)

Following the above-mentioned general procedure, 7-Hydroxy-4-(trifluoromethyl)-coumarin (0.90 g, 3.911 mmol) gave a crude product (1.20 g) which was fractionated on silica (200 g) with ether/chloroform (1:4). The residue (392 mg) from the third fraction was further purified by fractionating on silica (100 g) with ether. The first fraction then collected gave a residue (295 mg, 24.4%) which upon recrystallised in ethyl acetate/hexane (1:3) gave (16) as white needle-shaped crystals (160 mg).

Analytical data were as follows:

M.p. 165–168° C.; R$_f$s=0.67 (ether), 0.24 (ether/chloroform, 1:4); vmax (KBr) 3360, 3240, 3100, 1720, 1620, 1380, 1160 cm$^{-}$; $\delta_H$ (acetone-d$_6$) 6.995 (1H, s, C-3-H), 7.461 (1H, dd, $J_{C-8-H,\ C-6-H}$=2.8 Hz and $J_{C-5-H,\ C-6-H}$=8.1 Hz, C-6-H), 7.478 (1H, s, C-8-H), 7.53 (2H, br s, D$_2$O exchanged, —NH$_2$) and 7.89 (1H, m, C-5-H). $^1$H-NMR spectrum of (16) in DMSO-d$_6$/CDCl$_3$ (ca. 1:15) showed partial decompostion to the starting coumarin. MS: m/z (E.I., rel. intensity) 309.0 (2.6), 230.0(77), 202.0(100), 183.5(5), 173.0(10), 69.0(33). Acc. MS: m/z 308.9874, C$_{10}$H$_6$F$_3$NO$_5$S requires 308.9919. Found: C, 38.8; H, 1.85; N, 4.53. C$_{10}$H$_6$F$_3$NO$_5$S requires C, 38.84; H, 1.96; N, 4.53%.

Preparation of 7-(Sulphoxy)-4-Methylcoumarin, sodium salt (12)

Figure 3:
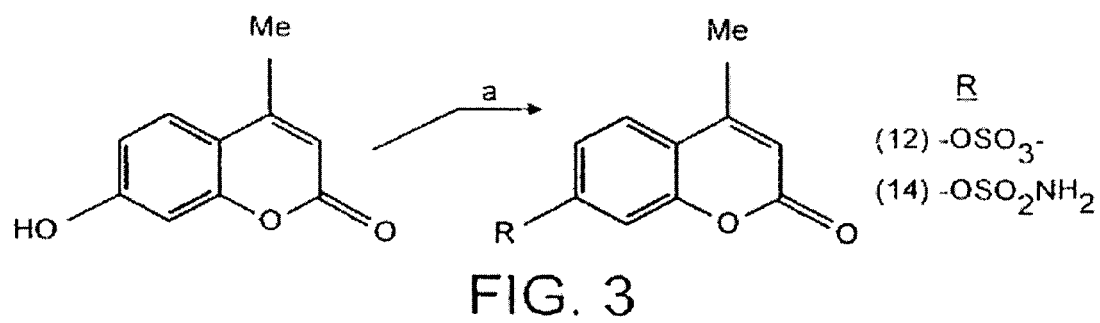
FIG. 3 shows the sulphation of 7-hydroxy-4-methylcoumarin; pyridine/$SO_3$-pyridine complex, NaOH in MeOH (Route a)

To a solution of 7-hydroxy-4-methylcoumarin (1.0 g, 5.676 mmol) in dried pyridine (20 ml) under an atmosphere of N$_2$ [FIG. 3] was added sulphur trioxide-pyridine complex (1.8 g, 11.35 mmol, 2 equiv.) and the reaction mixture was stirred overnight; After removal of pyridine, methanol (20 ml) was added to the creamy syrup obtained and the resulting light-yellow solution was basified (pH~8) by dropwise addition of sodium hydroxide in methanol (1 M, ca. 18 ml). The bright yellow suspension formed was filtered and the precipitated washed with more methanol. The filtrate was then concentrated to 30–40 ml and ether (total 120 ml) was added in portions until precipitation completed. The light beige precipitate was collected (711 mg) and 582 mg of which was recrystallised in methanol/ether (1:1) to give (12) as light creamy yellow crystals (335 mg).

Analytical data were as follows:

M.p. 172–175° C. (dec.); R$_f$s=0.51 (methanol/ethyl acetate, 1:3), 0.67 (methanol/ether, 1:3); vmax (KBr) 3500 (br), 3080, 1680, 1610, 1560, 1300, 1260, 1050 cm$^{-1}$; $\delta_H$ (DMSO-d$_6$) 2.407 (3H, s, —CH$_3$), 6.269 (1H, s, C-3-H), 7.20 (2H; m, C-6-H and C-8-H), and 7.695 (1H, d, $J_{C-6-H,\ C-5-H}$=8.8 Hz, C-5-H). MS: m/z (+ve ion FAB in m-NBA, rel. intensity) 176(100, NBA+Na$^+$). MS: m/z (–ve ion FAB in m-NBA, rel. intensity) 175.1(14, M–Na$^+$—SO$_3$), 255.0 (100, M–Na$^+$), 408.0 (8, M–Na$^+$+NBA), 431.0 (15, M+153), 444.0(20), 533.0(15). 230.0(77), 202.0(100), 183.5 (5), 173.0(10), 69.0(33). Acc. MS: m/z (–ve ion FAB in glycerol, rel. intensity) 254.9982(25), C$_{10}$H$_7$O$_6$S requires 254.9963. Found: C, 40.3; H, 2.92. C$_{10}$H$_7$O$_6$SNaS.H$_2$O requires C, 40.55; H, 3.06%. HPLC [Spherisorb ODS5, 25×4.6 mm; Mobile phase: MeOH/H$_2$O (70:30), Flow rate: 1 ml/min; $\lambda_{max}$: 316 nm]: t$_R$=1.5 min, c.f. 7-hydroxy-4-methylcoumarin, 3.6 min.

Other data were as follows:

Compound 12 is stable in bases such as sodium hydroxide in methanol but not in acidic conditions. In addition, incomplete basification of the reaction mixture with sodium hydroxide in methanol (<3 equivalents) leads to decomposition of (12). Two equivalents of sodium hydroxide are required for consuming excess sulphur trioxide-pyridine complex to yield the neutral sodium sulphate. Insufficient amount of sodium hydroxide will therefore lead to the formation of sodium hydrogen sulphate which is acidic. Compound 12 appears labile to high temperature as one experiment has shown complete decomposition to 7-hydroxy-4-methylcoumarin after heating (12) as solid at 90° C. for 4 h.

In Vitro Tests

The above-mentioned coumarin sulphamates were tested for their ability to inhibit E1-STS activity using intact MCF-7 breast cancer cells or placental microsomes (100,000 g fraction) essentially as previously described.

To examine whether compound (12) could act as a substrate for E1-STS, 100 μg of the compound was incubated for 1 hour with placental microsomes in the absence or presence of EMATE (10 μM). The unconjugated coumarin formed at the end of the incubation was extracted with diethyl ether. After evaporation of solvent, the residue was examined by TLC using ethyl acetate/methanol (80:20) as eluent, in which the coumarin sulphate (12) and 7-hydroxy-4-methylcoumarin had $R_f$ values of 0.79 and 0.95 respectively. Only unconjugated 7-hydroxy-4-methylcoumarin was detected after incubation of compound (12) with placental microsomes. The inclusion of EMATE in the reaction mixture reduced the hydrolysis of compound (12) by E1-STS, indicating that the coumarin sulphate is indeed a substrate for the sulphatase.

Figure 5:
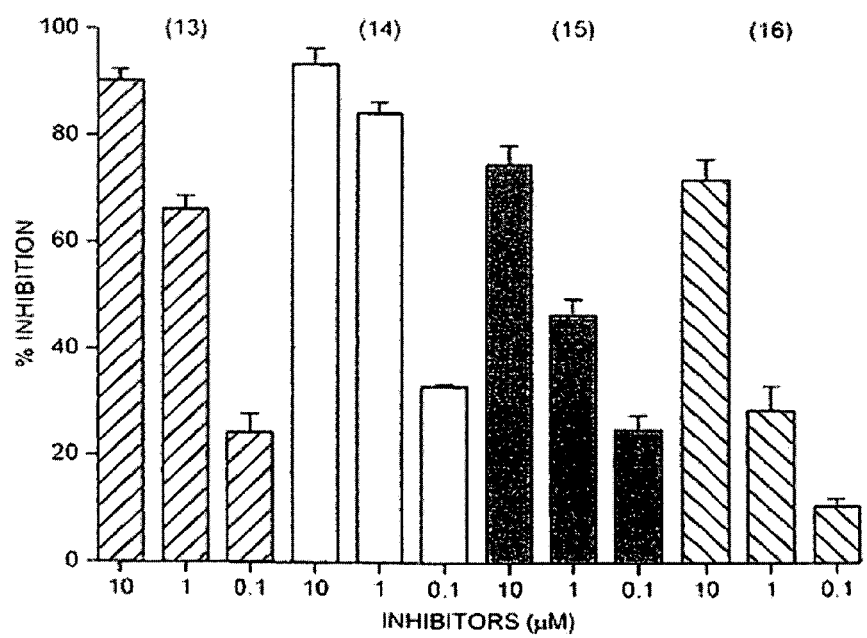
FIG. 5 shows the dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16)

The dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16) can be seen from FIG. 5. Assays were performed essentially as previously described (7, 8) Monolayers of intact MCF-7 cells in 25 cm³ flasks were incubated for 20 h at 37° C. with [³H]oestrone sulphate (2 nM) and coumarin sulphamates at 0.1–10 μM. Oestrone sulphatase activity was determined by measuring the total amount of ³H-labeled oestrone and oestradiol formed. Sulphatase activity in untreated cells was 100–200 fmol/20 h/10⁶ cells. Each point represents the mean±s.d. of triplicate measurements.

The free parent coumarins of all coumarin sulphamates prepared showed little or no E1-STS inhibitory activity when tested up to 10 μM. However, in contrast, all four coumarin sulphamates (compounds 13–16) inhibited oestrone sulphatase inhibitory activity in a dose-dependent manner (FIG. 5) and the inhibition at 10 μM ranged from 71.5% for compound 16 to 93.3% for compound 14. The IC$_{50}$ for inhibition of E1-STS by compound 14, the most effective inhibitor, measured using intact MCF-7 cells was 380 nM.

Figure 6:
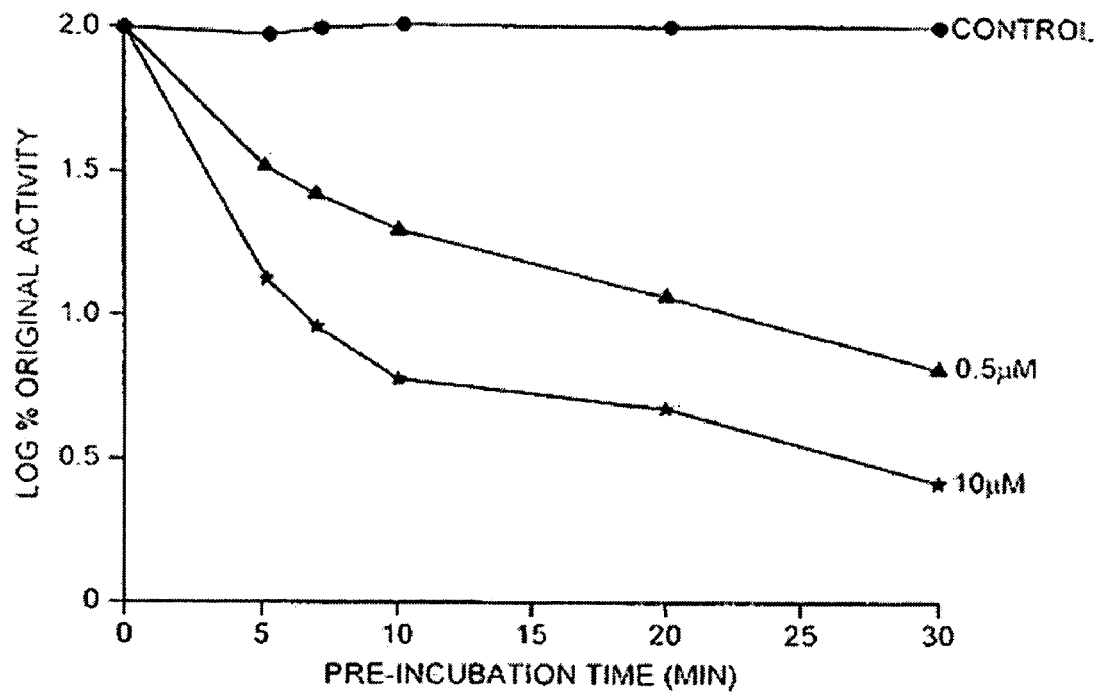
FIG. 6 shows the time-dependent and the concentration-dependent inactivation of oestrone sulphatase by 4-methyl-coumarin-7-O-sulphamate (14)

The time- and concentration-dependent inactivation of oestrone sulphatase by 4-methylcoumarin-7-O-sulphamate (14) can be seen from FIG. 6. Placental microsomes (200 μg) were preincubated with (14) (control, ●; 0.5 μM, ∆ and 10 μM, ★) for 0–30 min at 37° C. followed by incubation with dextran-charcoal for 10 min at 4° C. Dextran-charcoal was sedimented by centrifugation and portions of the supernatants were then incubated with [³H]oestrone sulphate (20 μM) for 1 h at 37° C. to assess remaining sulphatase activity. Duplicate experiments were run at each concentration, but assays for residual activity were taken at different times in each experiment.

As with EMATE, compound 14 inhibited E1-STS activity in a time- and concentration-dependent manner in a biphasic fashion (FIG. 6), indicating a similar mechanism of action (potential chemical modification of two active site residues). At 10 μM, compound 14 reduced the original E1-STS activity by 95% after preincubating the enzyme with the inhibitor for 20 min.

Additional experiments revealed that compound 14 inhibited placental microsomal DHA-STS activity by 93.6% at the same concentration.

In Vivo Tests

In order to examine if compound 14 possessed oestrogenic activity and also to test its ability to inhibit E1-STS in vivo, it was administered to rats (1 mg/kg subcutaneously, in propylene glycol for 5 days) 14 days after ovariectomy had been performed.

Administration of compound 14 did not result in any significant increase in the uterine weight in these rats (data not shown), showing that compound 14 showed reduced oestrogenic agonist properties. The E1-STS activity in the uteri obtained from these animals was inhibited by 89.4% compared with the activity in untreated animals.

Preliminary data also demonstrate potent oral activity in rats for compound 14, similar to that observed for EMATE.

In addition to these in vivo results, another series of rats (each weighing approximately 200 g) received 4-methyl coumarin-7-0-sulphamate (compound 14) orally in propylene glycol either as a single dose (SD) or daily for seven days (Multiple Dose, MD).

Inhibition of sulphatase activity was assessed in white blood cells (wbcs) that were collected after a SD or MD. Sulphatase activity was assayed using labelled oestrone sulphate as the substrate and measuring the release of oestrone.

Figure 7:
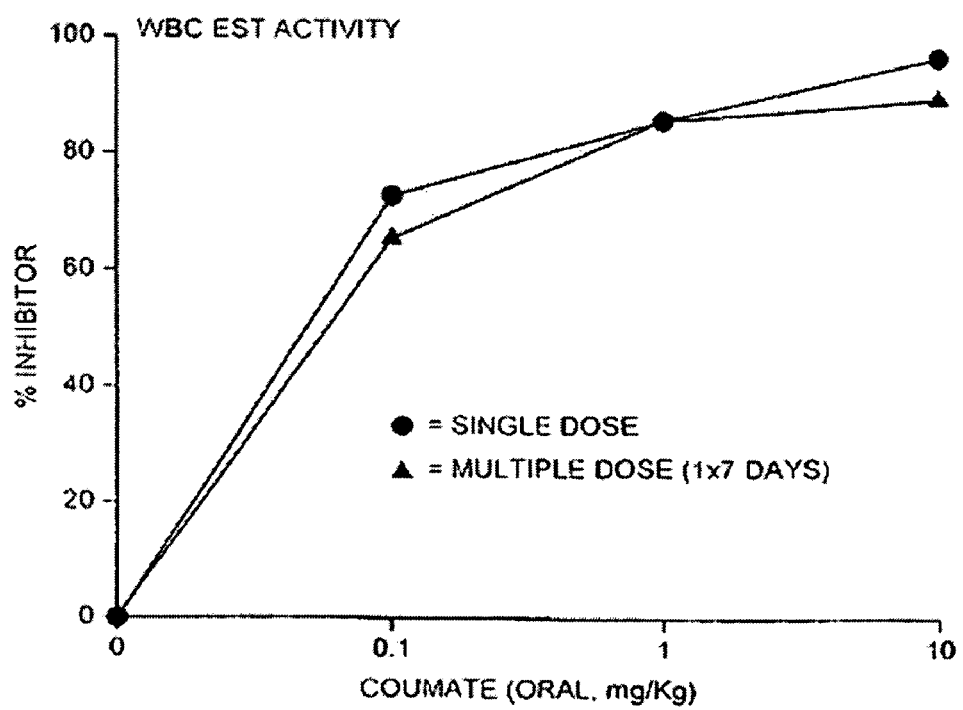
FIG. 7 is a graph showing the inhibition of sulphatase activity as assessed in white blood cells.
Figure 8:
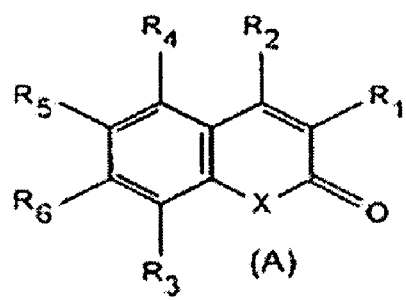
FIG. 8 presents Formulae (A), (B), (C), (D), (E), (F), (G) and (H).
Figure 8:
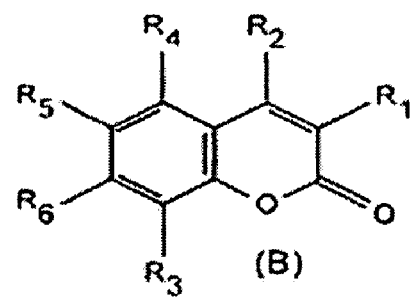
Figure 8:
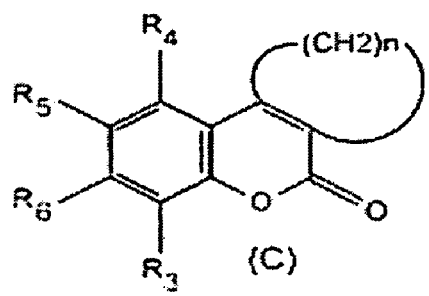
Figure 8:
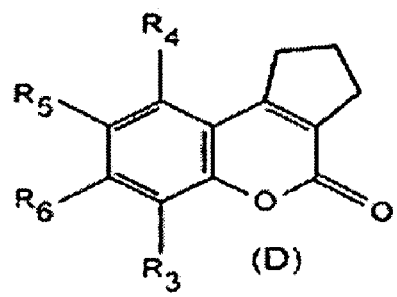
Figure 8:
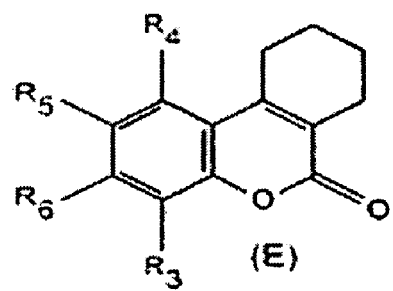
Figure 8:
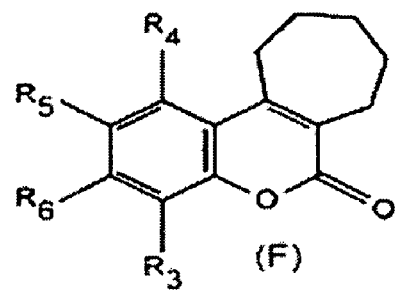
Figure 8:
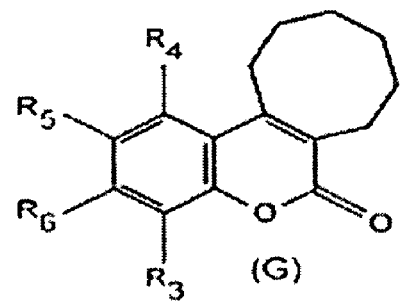
Figure 8:
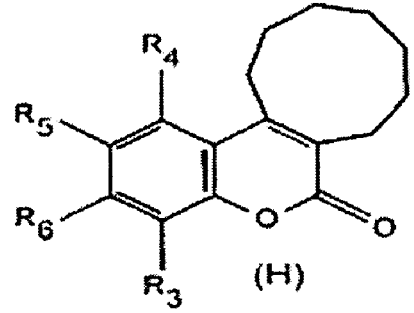
Figure 9:
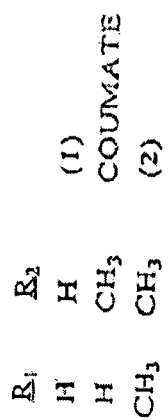
FIG. 9. Structures of EMATE, coumarin 7-O-sulphamate (1), COUMATE and 3,4-dimethylcoumarin 7-O-sulphamate (2).
Figure 9:
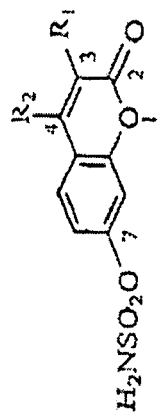
Figure 9:
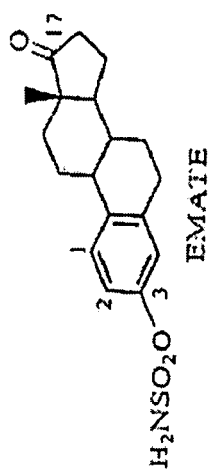
Figure 10:
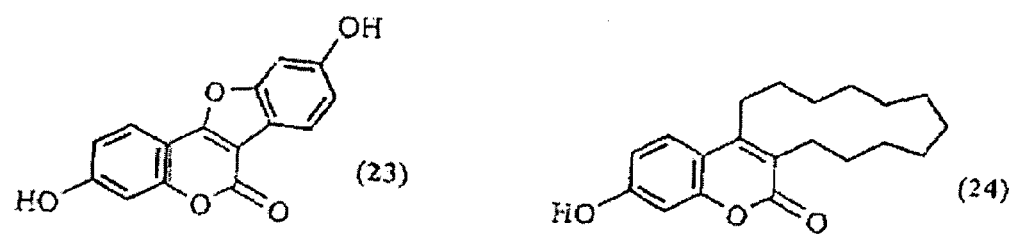
FIG. 10. Structures of coumestrol (23) and 6613COUMARIN (24).

The results are shown in FIG. 7 and in the Table below:

| Dose mg/kg | % Inhibition | |
| --- | --- | --- |
| | SD | MD |
| 0.1 | 72 | 65 |
| 1.0 | 85 | 85 |
| 10.0 | 96 | 89 |

Similar results were found with liver cells.

Compound 14 therefore demonstrates potent oral activity.

Further example compounds are as follows:

The following compounds of the present invention are made and are found to be steroid sulphatase inhibitors in accordance with the present invention.

Compounds 17a–17o

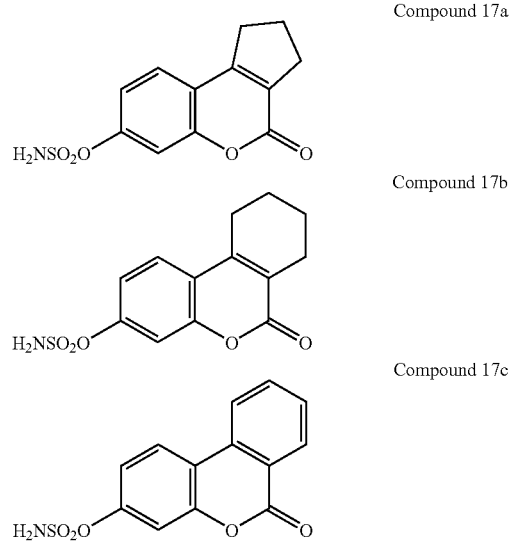

Compound 17a

Compound 17b

Compound 17c

-continued
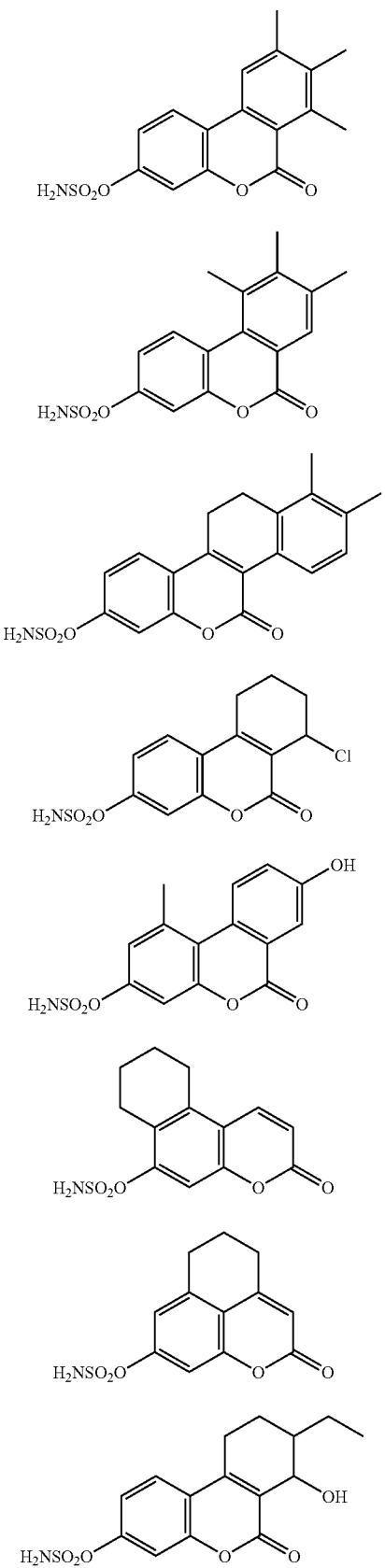
Compound 17d
Compound 17e
Compound 17f
Compound 17g
Compound 17h
Compound 17i
Compound 17j
Compound 17k
-continued
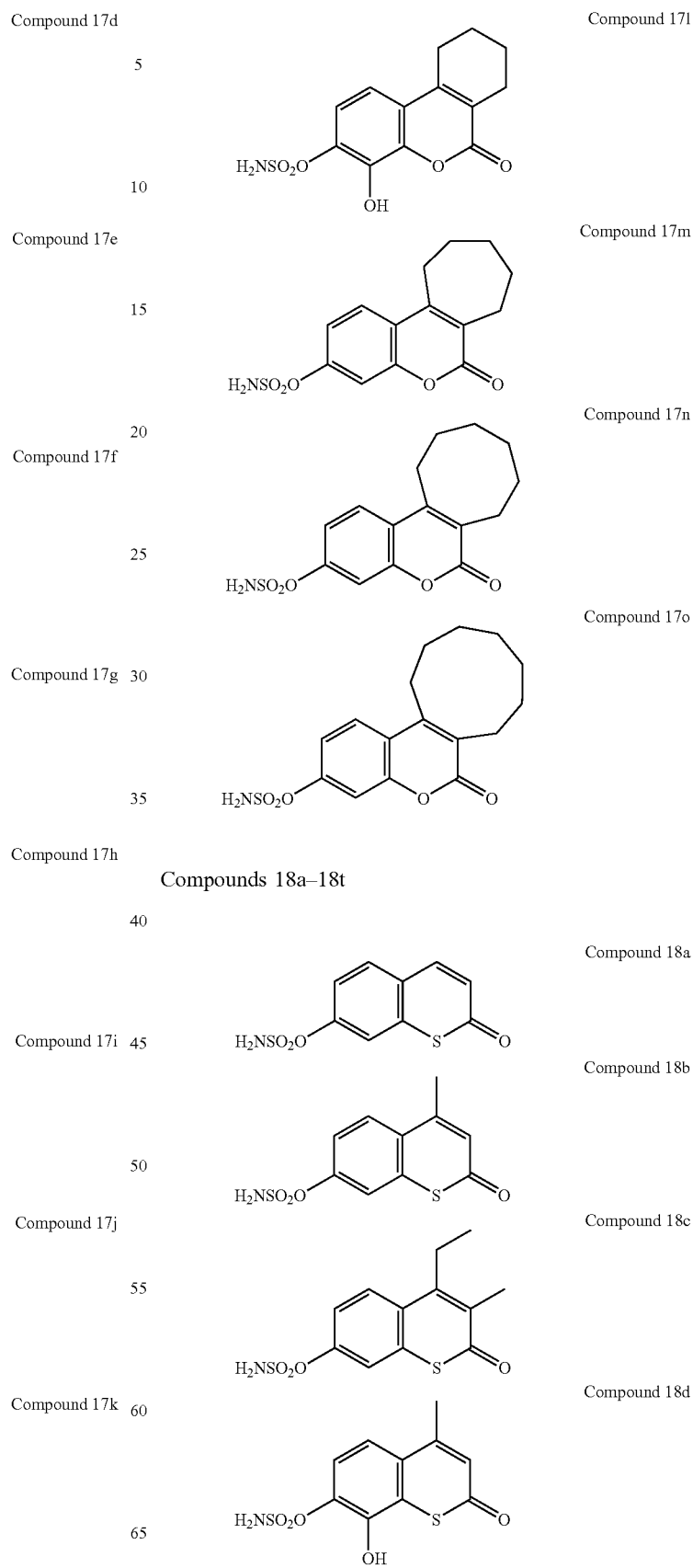
Compound 17l
Compound 17m
Compound 17n
Compound 17o
Compounds 18a–18t
Compound 18a
Compound 18b
Compound 18c
Compound 18d -continued
Compound 18e
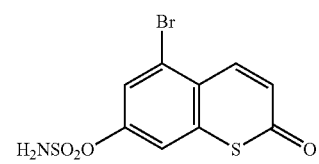
Compound 18f
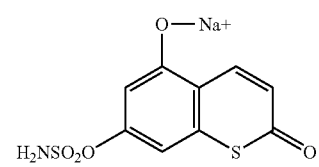
Compound 18g
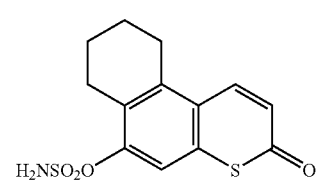
Compound 18h
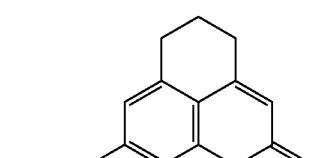
Compound 18i
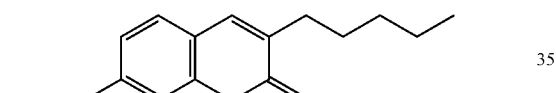
Compound 18j
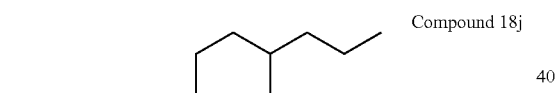
Compound 18k
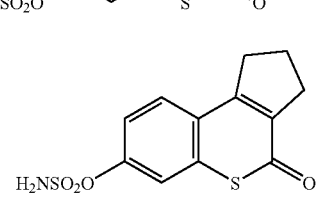
Compound 18l
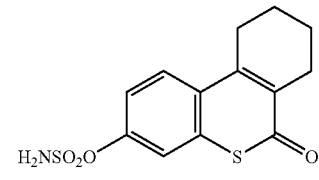
Compound 18m
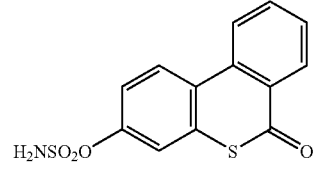
-continued
Compound 18n
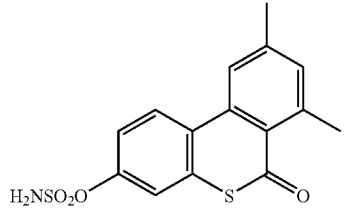
Compound 18o
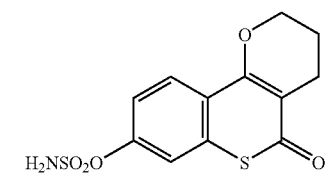
Compound 18p
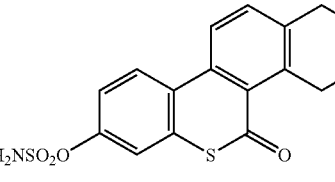
Compound 18q
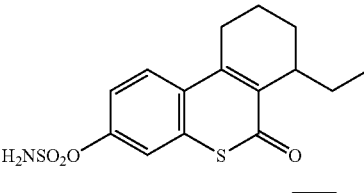
Compound 18r
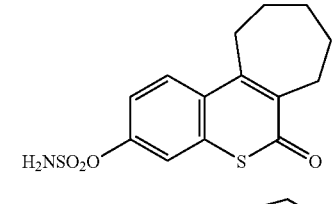
Compound 18s
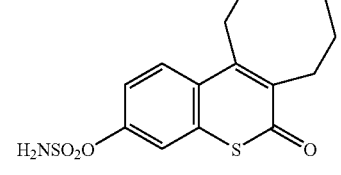
Compound 18t
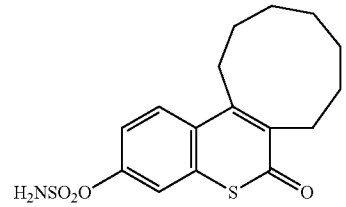
Compounds 19a–19t
Compound 19a
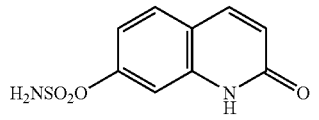

-continued
Compound 19b
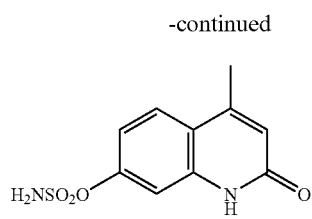
Compound 19c
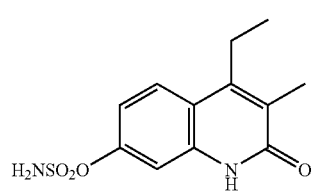
Compound 19d
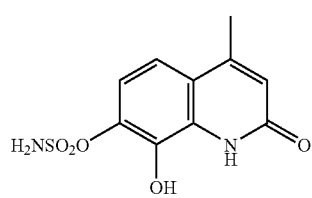
Compound 19e
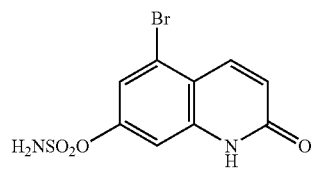
Compound 19f
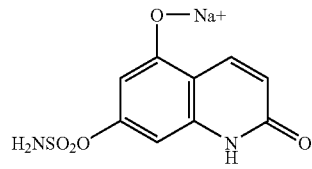
Compound 19g
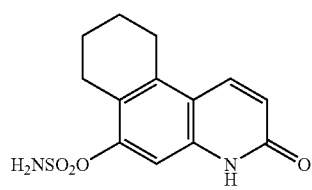
Compound 19h
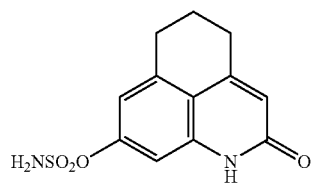
Compound 19i
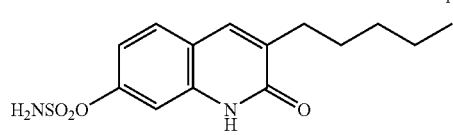
-continued
Compound 19j
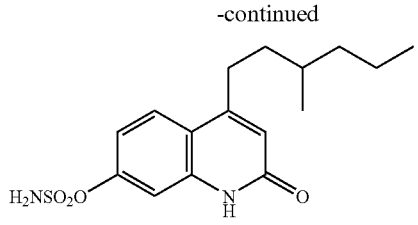
Compound 19k
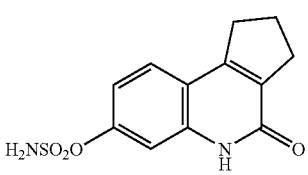
Compound 19l
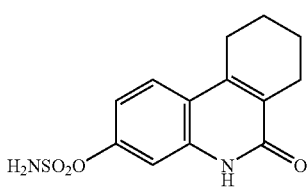
Compound 19m
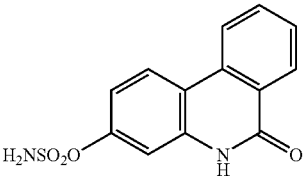
Compound 19n
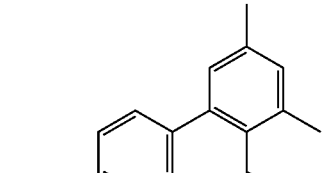
Compound 19o
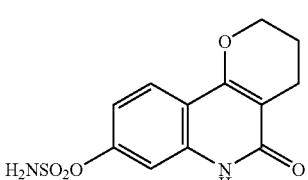
Compound 19p
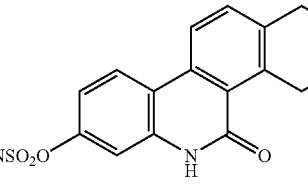
Compound 19q
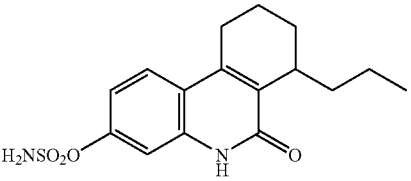

-continued
Compound 19r
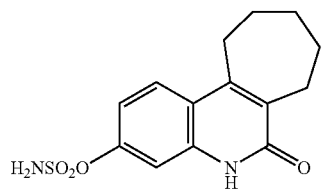
Compound 19s
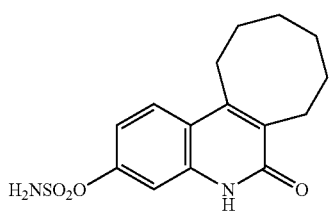
Compound 19t
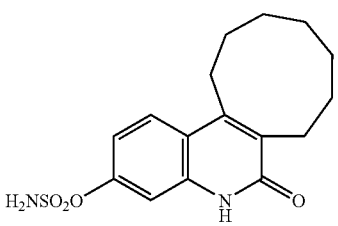
Compounds 20a–20n
Compound 20a
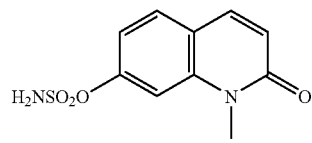
Compound 20b
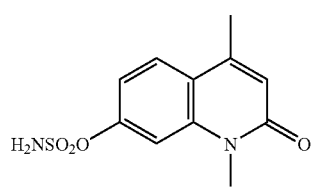
Compound 20c
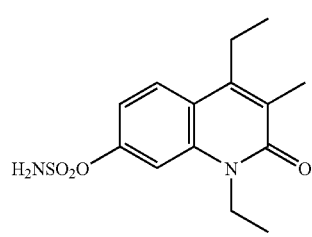
Compound 20d
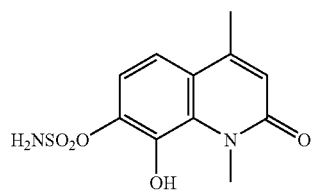
-continued
Compound 20f
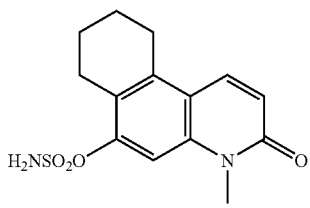
Compound 20g
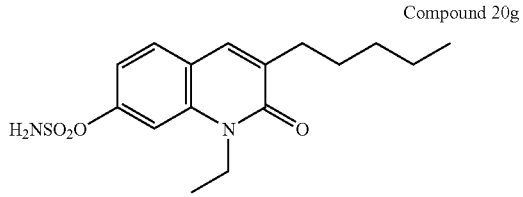
Compound 20h
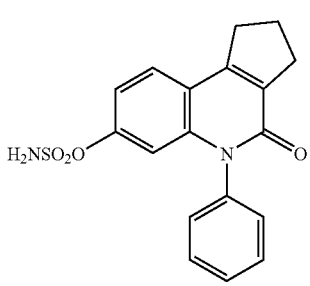
Compound 20i
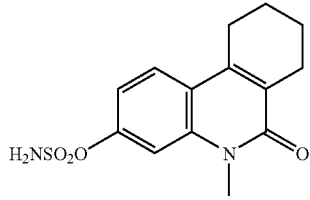
Compound 20j
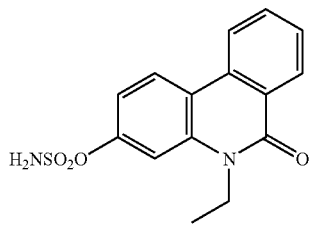
Compound 20k
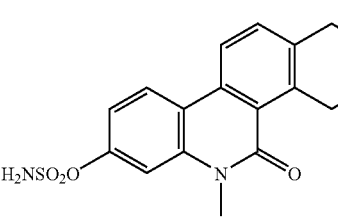
Compound 20l
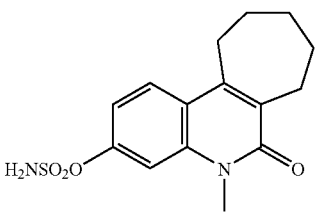

-continued
Compound 20m
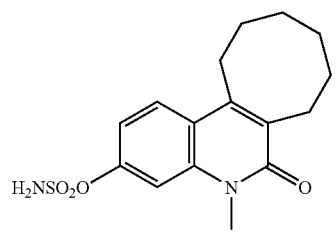
Compound 20n
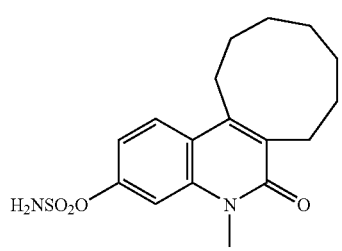
Compounds 21a–21t
Compound 21a
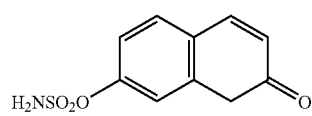
Compound 21b
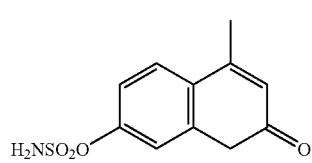
Compound 21c
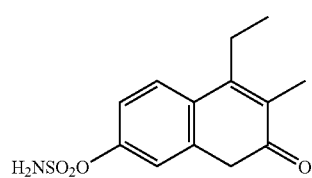
Compound 21d
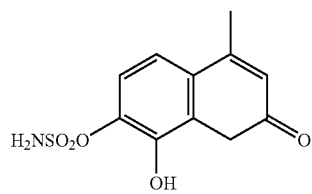
Compound 21e
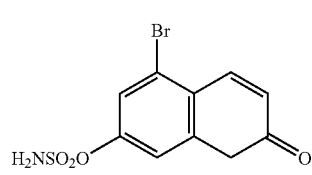
Compound 21f
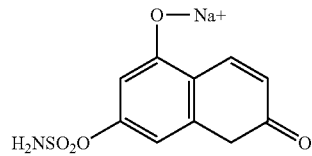
-continued
Compound 21g
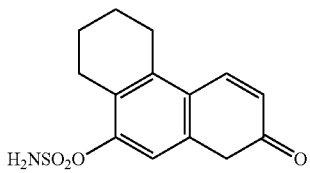
Compound 21h
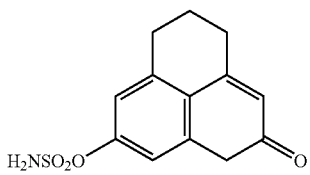
Compound 21i
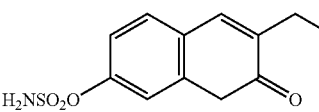
Compound 21j
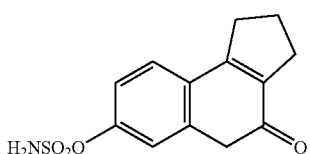
Compound 21k
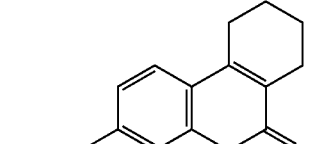
Compound 21l
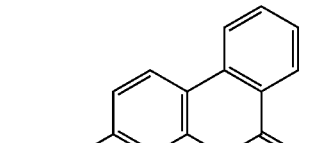
Compound 21m
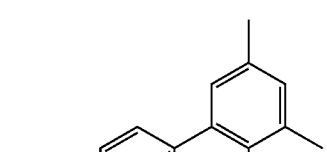
Compound 21n
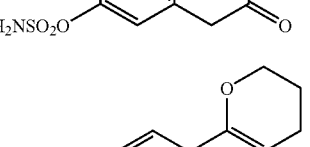
Compound 21o
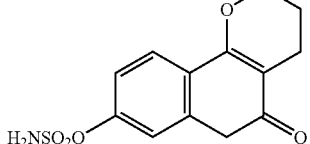

-continued
Compound 21p
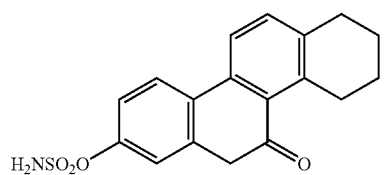
Compound 21q
Compound 21r
Compound 21s
Compound 21t
Compounds 22a–22n
Compound 22a
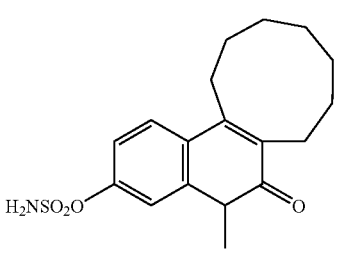
Compound 22b
-continued
Compound 22c
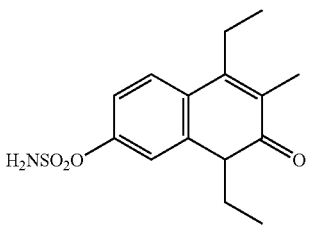
Compound 22d
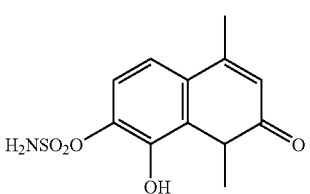
Compound 22f
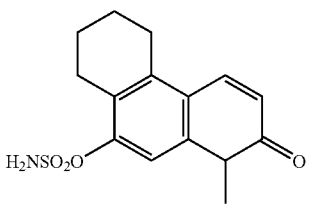
Compound 22g
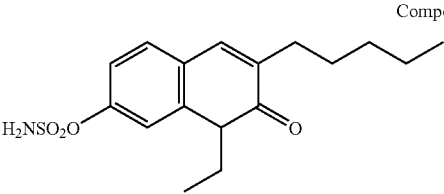
Compound 22h
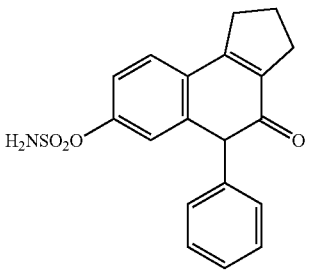
Compound 22i
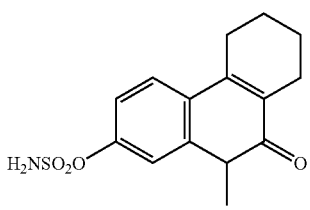
Compound 22j
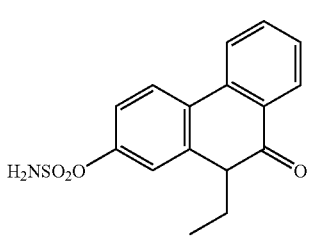

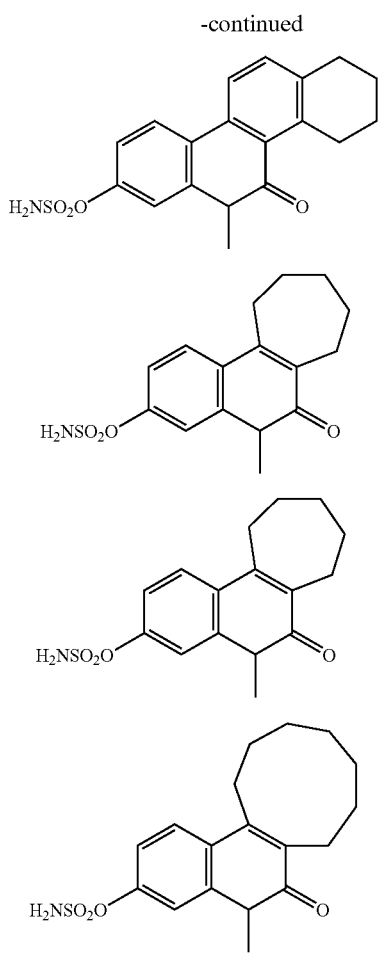

Compound 22k

Compound 22l

Compound 22m

Compound 22n

The synthesis and biological activity of futher compounds in accordance with the present invention are set out in Appendix I.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

REFERENCES (1) Santner, S. J.; Feil, P. D.; Santen, R. J. In situ oestrogen production via the oestrone sulphatase pathway in breast tumors: relative importance vs. the aromatase pathway. *J. Clin. Endocrinol. Metab.* 1984, 59, 29–33.

(2) Yamamoto, T.; Kitawaki, J.; Urabe, M.; Honjo, H.; Tamura, T.; Noguchi, T.; Okada, H.; Sasaki, H.; Tada, A.; Terashima, Y.; Nakamura, J.; Yoshihama, M. Oestrogen productivity of endometrium and endometrial cancer tissue—influence of aromatase on proliferation of endometrial cancer cells. *J. Steroid Biochem. Mol. Biol.* 1993, 44, 463–468.

(3) Santen, R. J.; Santner, S. J.; Davis, B.; Veldhuis, J.; Samojilik, E.; Ruby, E. Aminogluthethimide inhibits extraglandular oestrogen production in post-menopausal women with breast carcinoma. *J. Clin. Endocrinol. Metab.* 1978, 47, 1257–1265.

(4) Reed, M. J.; Lai, L. C.; Owen, A. M.; Singh, A.; Coldham, N. G.; Purohit, A.; Ghilchik, M. W.; Shaikh, N. A.; James, V. H. T. Effect of treatment with 4-hydroxyandrostenedione on the peripheral conversion of androstenedione to oestrone and in vitro tumour aromatase activity in postmenopausal women with breast cancer. *Cancer Res.* 1990, 50, 193–196.

(5) Ruder, H. J.; Loriaux, D. L.; Lipsett, M. B. Oestrone sulphate: production rate and metabolism in man. *J. Clin. Invest.* 1972, 51, 1020–1023.

(6) James, V. H. T.; McNeill, J. M.; Lai, L. C.; Newton, C. J.; Ghilchik, M. W.; Reed, M. J. Aromatase activity in normal breast and breast tumor tissues: in vivo and in vitro studies. *Steroids* 1987, 50, 269–279.

(7) Howarth, N. M.; Purohit, A.; Reed, M. J.; Potter, B. V. L. Oestrone sulphamates: potent inhibitors of oestrone sulphatase with therapeutic potential. *J. Med. Chem.* 1994, 37, 219–221.

(8) Purohit, A.; Williams, G. J.; Howarth, N. M.; Potter, B. V. L.; Reed, M. J. Inactivation of steroid sulphatase by an active site-directed inhibitor, oestrone-3-O-sulphamate. *Biochemistry* 1995, 34, 11508–11514.

(9) Purohit, A.; Dauvois, S.; Parker, M. G.; Potter, B. V. L.; Williams, G. J.; Reed, M. J. The hydrolysis of oestrone sulphate and dehydroepiandrosterone sulphate by human steroid sulphatase expressed in transfected COS-1 cells. *J. Steroid Biochem. Mol. Biol.* 1994, 50, 101–104.

(10) Dauvois, S.; Labrie, F. Androstenedione and androst-5-ene-3β,17β-diol stimulate DMBA-induced rat mammary tumours—role of aromatase. *Breast Cancer Res. Treat.* 1989, 13, 61–69.

(11) Purohit, A.; Williams, G. J.; Roberts, C. J.; Potter, B. V. L.; Reed, M. J. In vivo inhibition of oestrone sulphatase and dehydroepiandrosterone sulphatase by oestrone-3-O-sulphamate. *Int. J. Cancer* 1995, 63, 106–111.

(12) Woo, L. W. L.; Lightowler, M.; Purohit, A.; Reed, M. J.; Potter, B. V. L. Heteroatom-substituted analogues of the active-site directed inhibitor oestra-1,3,5(10)-trien-17-one-3-sulphamate inhibit oestrone sulphatase by a different mechanism. *J. Steroid Biochem. Mol. Biol.* 1996 (in press).

(13) Elger, W.; Schwarz, S.; Hedden, A.; Reddersen, G.; Schneider, B. Sulphamates of various oestrogens—prodrugs with increased systemic and reduced hepatic oestrogenicity at oral application. *J. Steroid Biochem. Mol. Biol.* 1995, 55, 395–403.

(14) Li, P. K; Rhodes, M. E.; Jagannathan, S; Johnson, D. A. Memory enhancement mediated by the steroid sulphatase inhibitor oestrone 3-O-sulphamate. *J. Endocrinol.* 1995, 144, Abstr. P155.

(15) Daynes, R. A.; Araneo, B. A.; Dowell, T. A.; Huang, K.; Dudley, D. Regulation of murine lymphokine production in vivo. 3. The lymphoid tissue micro-environment exerts regulatory influences over T-helper cell function. *J. Exp. Med.* 1990, 171, 979–996.

(16) Rook, G. A. W.; Hernandez-Pando, R.; Lightman, S. Hormones, peripherally activated prohormones and regulation of the TH1/TH2 balance. *Immunol. Today* 1994, 15, 301–303.

4-Ethyl-(4), 4-(n-propyl)-(6), 3-ethyl-4-methyl-(8), 4-methyl-3-(n-propyl)coumarin-7-O-sulphamate (11); the tricyclic derivatives 665COUMATE (13), 666COUMATE (15), 667COUMATE (17), 668COUMATE (20) and the tricyclic oxepin sulphamate (22) were synthesised. In a placental microsomes preparation, all of these analogues were found to be more active than COUMATE in the inhibition of oestrone sulphatase, with the most potent inhibitor being 667COUMATE which has an $IC_{50}$ of 8 nM, some 3-fold lower than that for EMATE (25 nM). In addition, 667COUMATE was also found to inhibit DHEA-sulphatase some 25-fold more potently than EMATE in a placental microsomes preparation. Like EMATE, 667COUMATE acts in a time- and concentration-dependent manner, suggesting that it is an active site-directed inhibitor. However, in contrast to EMATE, 667COUMATE has the important advantage of not being oestrogenic. In addition, we propose several diverse mechanisms of action for this active site-directed steroid sulphatase inhibitor in the light of recent publications on the crystal structures of human arylsulphatases A and B and the catalytic site topology for the hydrolysis of a sulphate ester.

The inhibitory activities of the 3-alkyl-4-methyl- and 4-alkylcoumarin sulphamates against E1-STS activity in placental microsomes are shown in Table 1. For the purpose of comparison, the inhibitory activities of 1, COUMATE and 2 obtained from our previous work [28] are also included. It is clear that all these derivatives (4, 6, 8 and 11) were found to be more potent E1-STS inhibitors than COUMATE. The substitution at the 3-position of the coumarin ring with alkyl groups of longer chain length proved to be more productive than that at the 4-position as shown by the overall higher potencies of the inhibitors in the former series. Although the methyl group at C4 of the inhibitors in the 3-alkyl series must also be a contributory factor to the higher potency observed, it is apparent that the hydrophobic interactions between the amino acids in the active site, which naturally recognise the steroid scaffold, and the alkyl substituents are more effective when these substitutents are placed at the C3 position of the coumarin ring. Since we have proposed that coumarin sulphamates are steroid sulphatase inhibitors by virtue of their structural mimicry of the A/B ring of EMATE, it is conceivable that the positioning of alkyl substituents with high rotational degrees of freedom at the 4-position of the coumarin ring may be counterproductive. The active site of steroid sulphatase, like many other enzymes with a steroid as substrate, is expected to have limited accommodation for substituents at the C1/C11/C12 edge of the steroid scaffold. For this reason, the relatively weaker inhibitions shown by the inhibitors in the 4-alkyl series can be attributed to their less favourable binding to the enzyme active site.

Table 1. Inhibition of oestrone sulphatase activity in placental microsomes by 4-alkyl coumarin sulphamates (4 and 6) and 3-alkyl-4-methylcoumarin sulphamates (8 and 11) at various concentrations. [$^3$H]Oestrone sulphate (4×10$^5$ dpm), adjusted to 20 μM with unlabeled substrate, with or without the inhibitor at various concentrations, was incubated with placental microsomes (125 μg of protein/mL) for 30 min. The product formed was isolated by extraction into toluene with [4-$^{14}$C]estrone (7×10$^3$ dpm) being used to monitor procedural losses. Each value represents the mean±s.d. of triplicate measurements. a)>90% at 50 μM. b) results reproduced from Ref. 28.

| Compound | % Inhibition ± S.D. of E1-STS activity in placental microsomes at various concentrations | | |
|---|---|---|---|
| | 0.1 μM | 1 μM | 10 μM |
| 1 (C3-H, C4-H)[a,b] | — | — | 78 ± 1 |
| COUMATE (C3-H, C4-Me)[b] | <10 | 63 ± 1 | 93 ± 1 |
| 2 (C3-Me, C4-Me)[b] | 35 ± 1 | 88 ± 2 | 97 ± 4 |
| 4 (C3-H, C4-Et) | 35 ± 1 | 88 ± 1 | >99 |
| 6 (C3-H, C4-n-propyl) | 42 ± 2 | 94 ± 1 | 96 ± 1 |
| 8 (C3-Et, C4-Me) | 57 ± 1 | 96 ± 1 | >99 |
| 11 (C3-n-propyl, C4-Me) | 83 ± 1 | 97 ± 1 | >99 |

Figure 11:
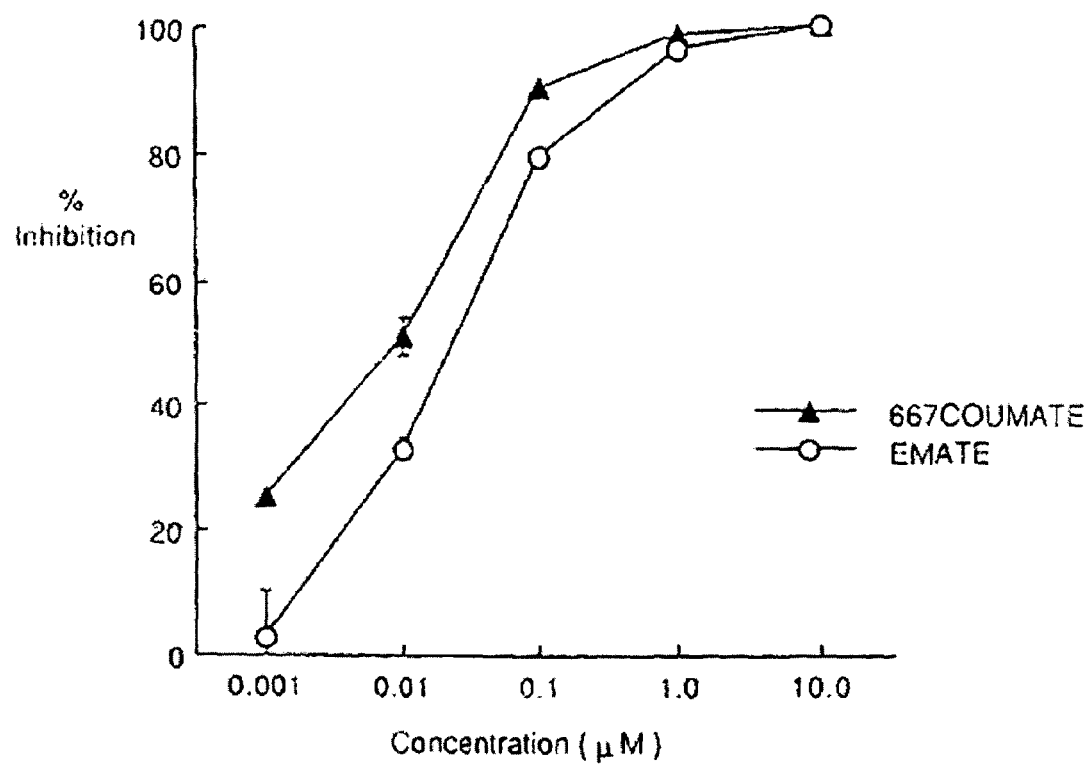
FIG. 11. Dose-response curves for inhibition of oestrone sulphatase activity in placental microsomes by 667COUMATE (17, ▲) and EMATE (O). Method as described for Table 1.
Figure 12:
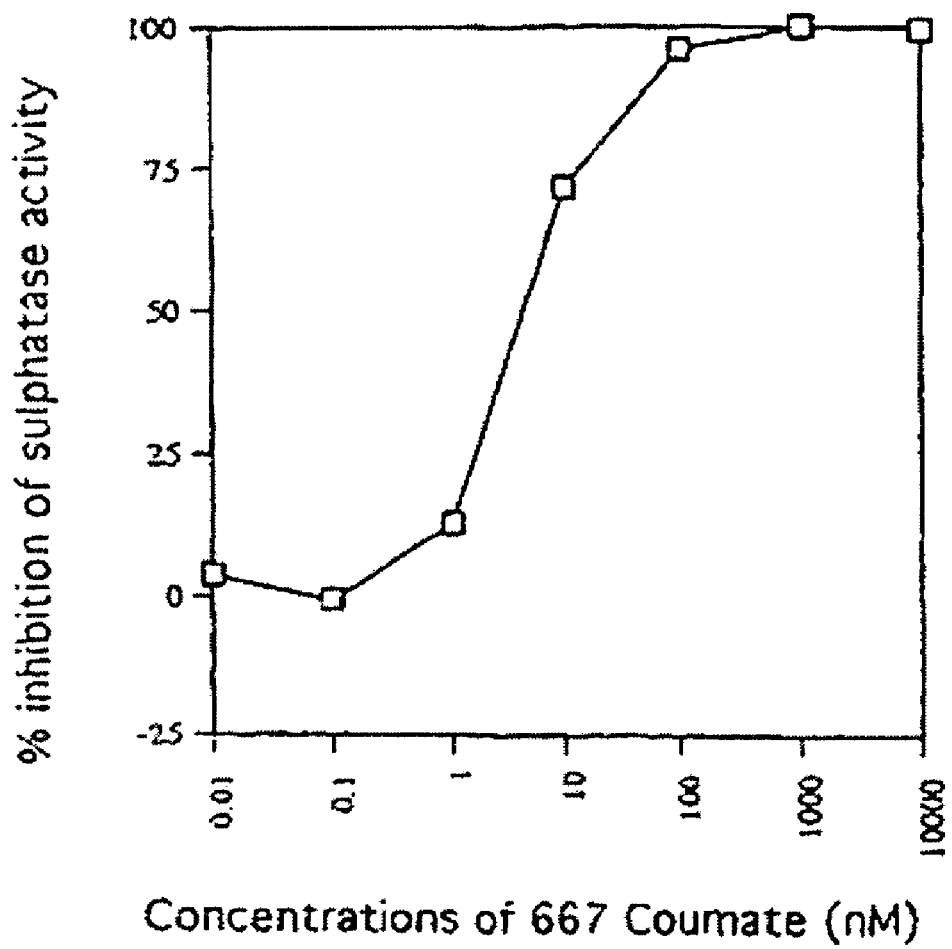
FIG. 12. Dose-response curves for inhibition of DHEA sulphatase activity in placental microsomes by 667COUMATE (17). Method as described for Table 1 except $^3$H-DHEAS ($4\times10^5$ dpm) adjusted to 20 μm with unlabelled DHEAS was used.

Our prediction that coumarin sulphamate analogues with substituents of increased hydrophobicity at the 3- and/or 4-positions should be more potent steroid sulphatase inhibitors has been further confirmed by the even higher potency observed in most of the tricyclic coumarin sulphamates, e.g. both 17 and 20 gave almost complete inhibition at 1 μM in a placental microsomes preparation (Table 2). The best inhibitor in this series is 17 (667COUMATE) whose $IC_{50}$ value for the inhibition of E1-STS activity in placental microsomes is 8 nM (FIG. 11) which is some three-fold more potent than EMATE in the same assay ($IC_{50}$=25 nM) (FIG. 11). Like EMATE, but much more effectively, 17 also inhibited the hydrolysis of DHEA-sulphate by DHEA sulphatase in a placental microsomes preparation (FIG. 12) with an $IC_{50}$ of 4.5 nM (c.f. 110 nM for EMATE [25]).

Table 2. Inhibition of oestrone sulphatase activity in placental microsomes by tricyclic coumarin sulphamates (13, 15, 17 and 20) and tricyclic oxepin sulphamate (22) at various concentrations. For details of the assay, refer to the legend of Table 1.

| Compound | % Inhibition ± S.D. of E1-STS activity in placental microsomes at various concentrations | | |
|---|---|---|---|
| | 0.01 μM | 0.1 μM | 1 μM |
| 13 (665COUMATE)[a] | <10 | 37 ± 1 | 91 ± 2 |
| 15 (666COUMATE)[a] | <10 | 63 ± 1 | 93 ± 1 |
| 17 (667COUMATE) | 48 ± 2 | 91 ± 1 | >99 |
| 20 (668COUMATE) | 17 ± 2 | 89 ± 1 | >99 |
| 22 | <10 | 31 ± 5 | 94 ± 2 |

Figure 13:
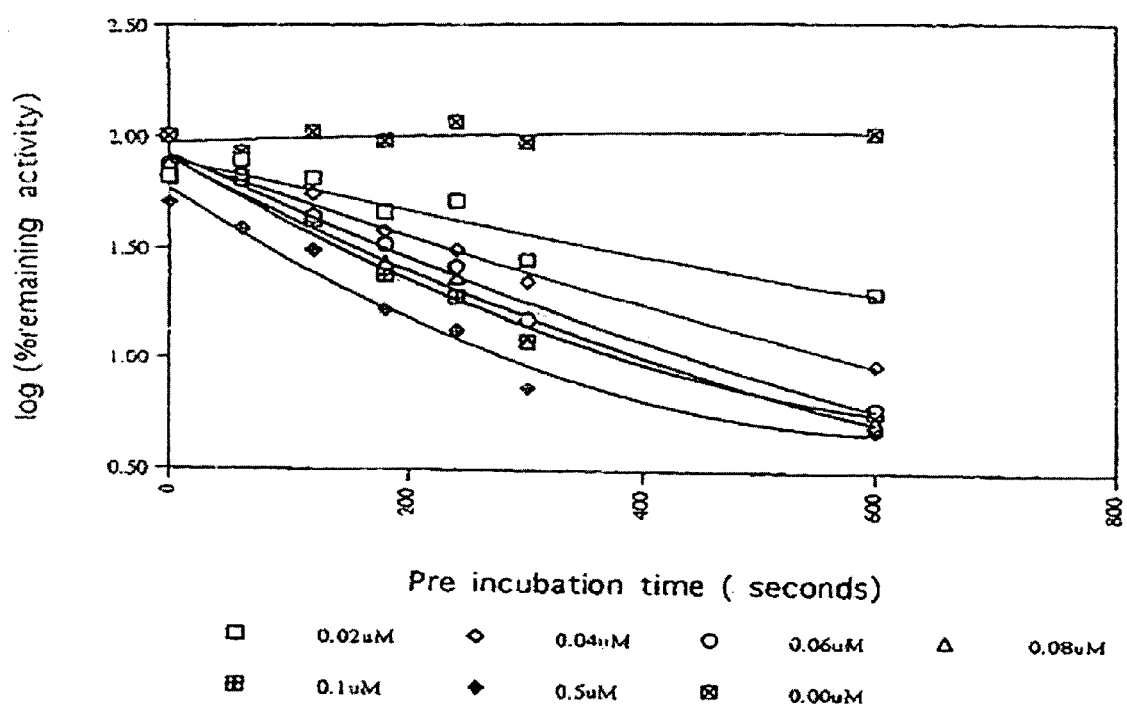
FIG. 13. Time- and concentration-dependent inactivation of oestrone sulphatase by 667COUMATE (17). Placental microsomes (200 μg of protein) were preincubated with the inhibitor at 0 to 0.5 μm for 0–10 min at 37° C. followed by incubation with dextran-charcoal for 10 min at 4° C. Dextran-charcoal was sedimented by centrifugation, and portions of the supernatants were then incubated with [$^3$H] estrone sulfate (20 μm) for 1 h at 37° C. to assess remaining sulfatase activity. Duplicate experiments were run at each concentration, but assays for residual activity were taken at different times in each experiment.
Figure 14:
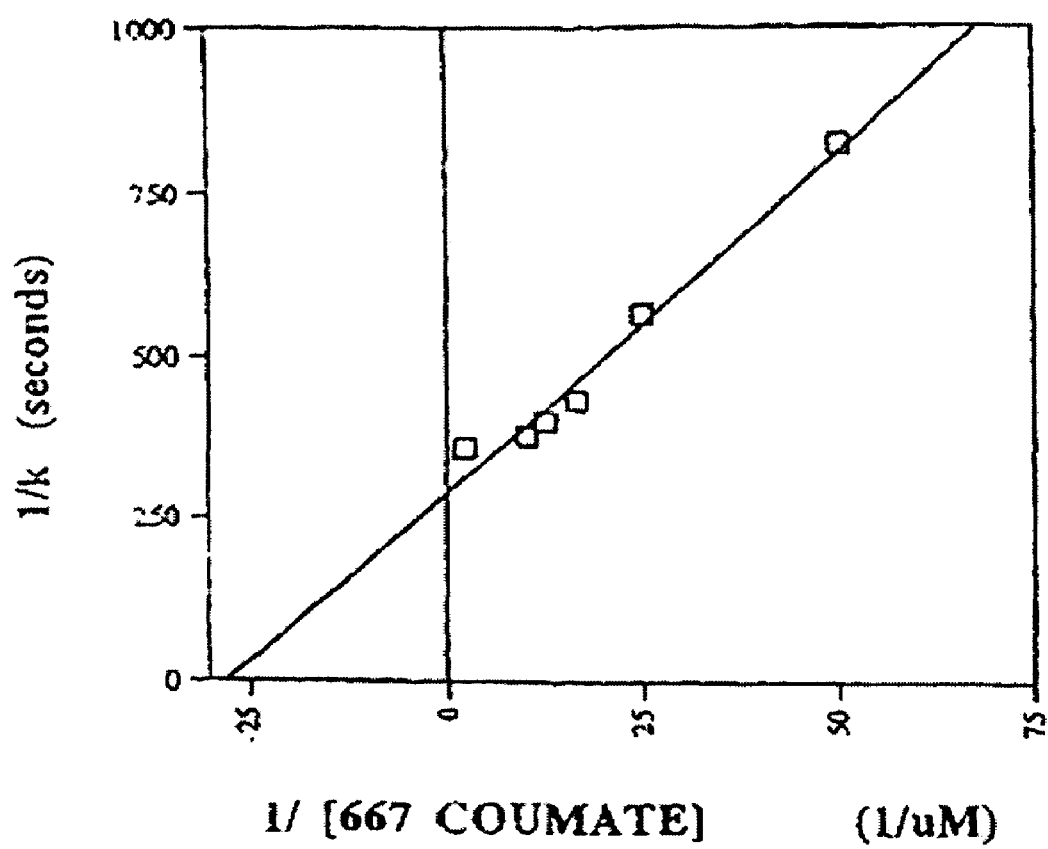
FIG. 14. Double reciprocal plot of inactivation rate constant versus 667COUMATE concentration.
Figure 15:
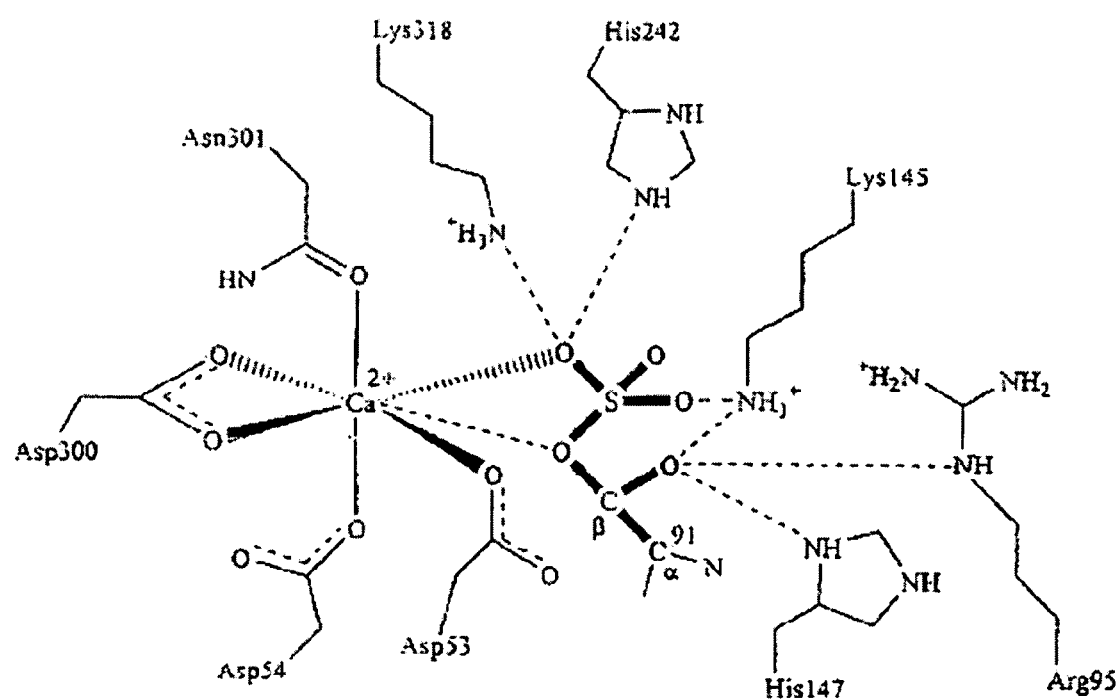
FIG. 15. Sketch view of the catalytic site of arylsulphatase B showing hydrogen-bonded interactions (dashed lines) that stabilize the sulphate ester. The seven coordinate metal ion is on the left. A salt-bridge interaction between Lys145 and the O (carboxyl) atom of Asp53, which is not coordinated to the metal ion, and a number of charges and double bonds are omitted from the figure for clarity (adapted from Ref. 40 with permission).
Figure 16:
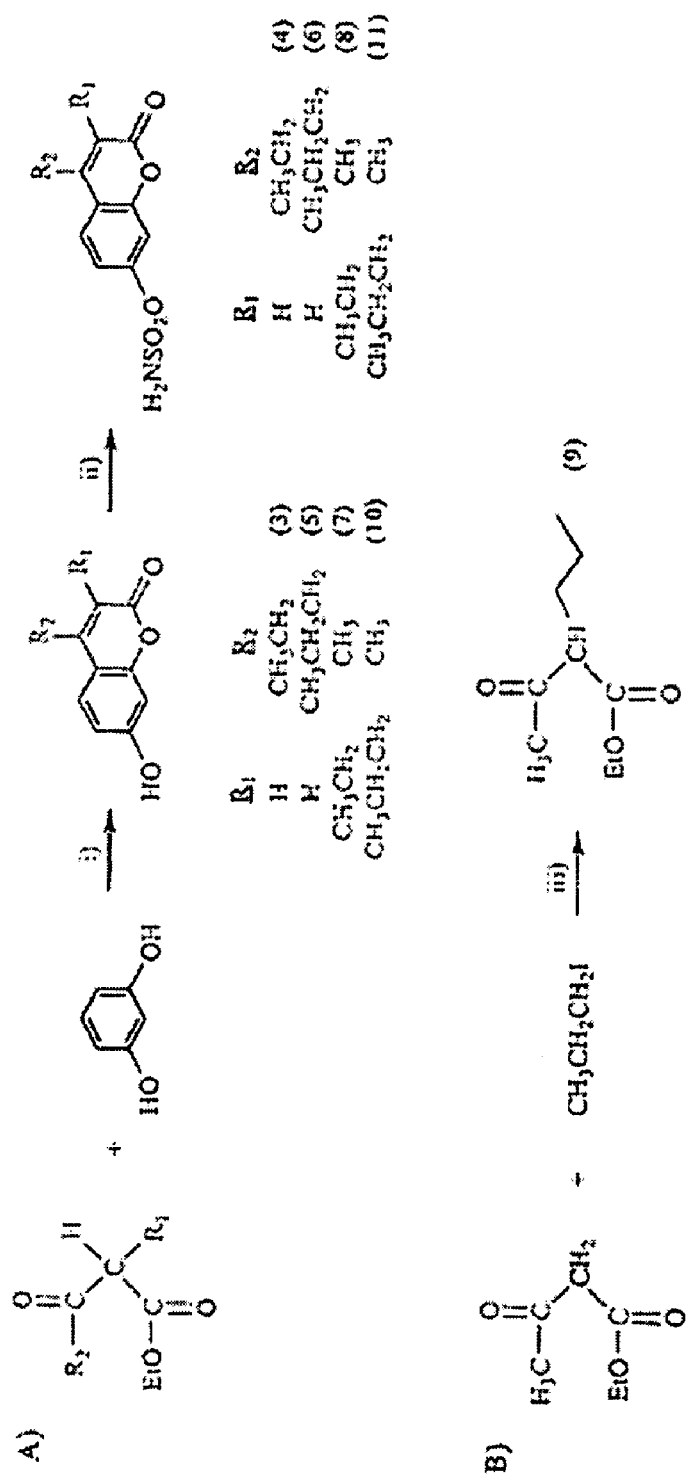
FIG. 16—Scheme 1. A) Structures and synthesis of coumarins (3, 5, 7 and 10) and their corresponding sulphamates (4, 6, 8 and 11). B) Synthesis of ethyl (2-n-propyl)acetoacetate (9). i) $CF_3COOH$/conc. $H_2SO_4$ (1:1), 0° C.→r.t.; ii) NaH/DMF, $H_2NSO_2Cl$; iii) $K_2CO_3$/(Bu)4N$^+$Cl$^-$×$H_2O$, r.t.
Figure 17:
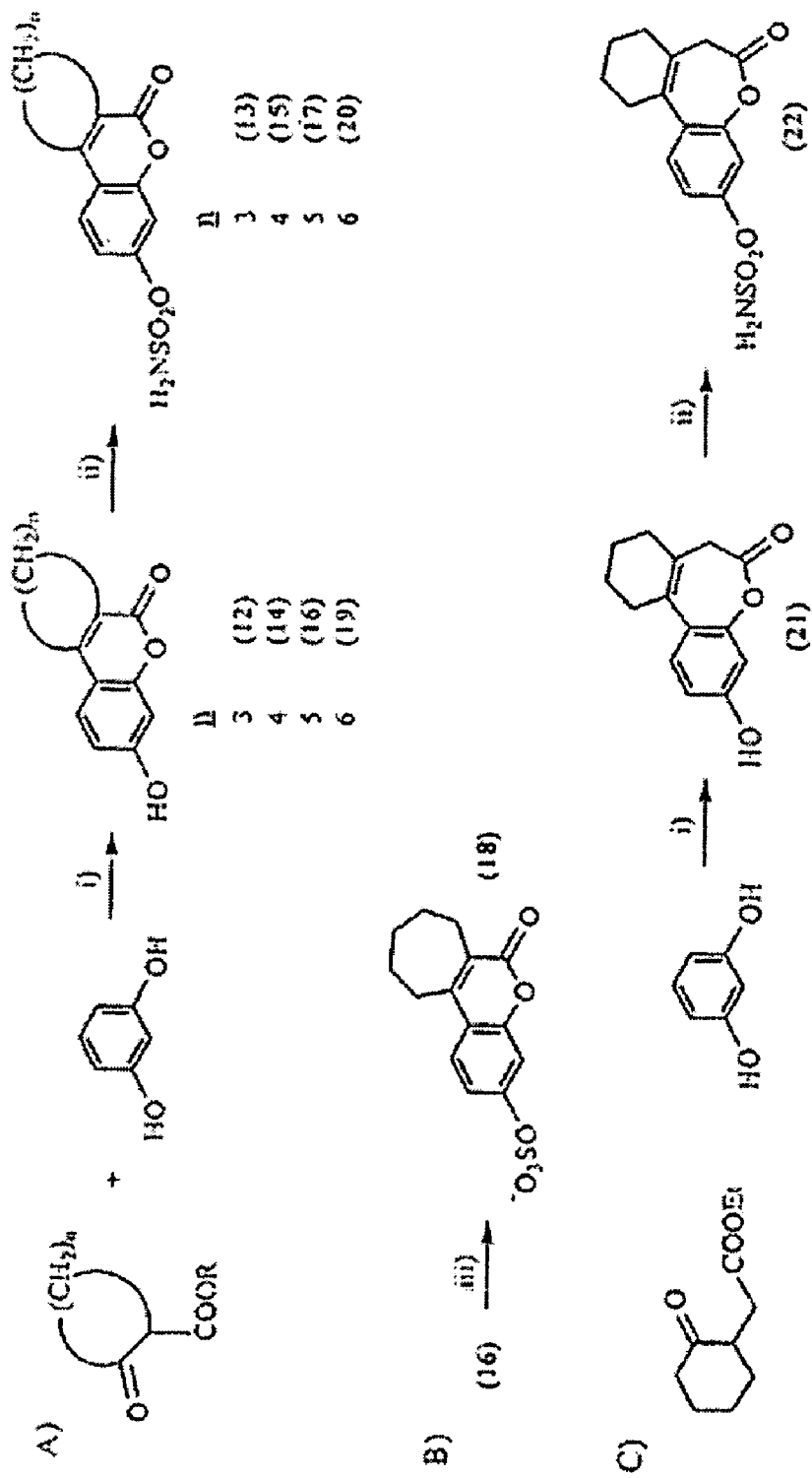
FIG. 17—Scheme 2. A) Structures and synthesis of tricyclic coumarins (12, 14, 16 and 19) and their corresponding sulphamates (13, 15, 17 and 20). B) Sulphation of coumarin 16. C) Synthesis of the tricyclic oxepin (21) and its sulphamate (22). i) $CF^3COOH$/conc. $H_2SO_4$ (1:1), 0° C.→r.t.; ii) NaH/DMF, $H_2NSO_2Cl$; iii) $Me_3NSO_3$, 1M NaOH (aq).

The time- and concentration-dependent inactivation of the E1-STS activity in placental microsomes by 17 is shown in FIG. 13. As with EMATE, the inhibition by 17 is biphasic, indicating that the inhibitor shares a similar mechanism of action to that proposed for EMATE, which we have postulated acts via irreversible sulphamoylation of one or more residues in the enzyme active site [28]. The double-reciprocal plot of the first-order rates of inactivation versus the concentrations of 17 is shown in FIG. 14. The apparent $K_i$ for 17 was found to be 40 nM which is significantly lower than that for EMATE (670 nM) [25]. This suggests that the lower $IC_{50}$ value observed for 17 in comparison with EMATE could be attributed to a higher affinity of 17 for the enzyme active site. As calculated by the method of Kitz and Wilson [49], the overall rate constant for the decrease in activity was found to be 3.45×10$^{-3}$ s$^{-1}$ for 17. To date, the only successful approach to the design of steroid sulphatase inhibitors which are more potent than EMATE, the benchmark inhibitor of this field, has been by incorporating hydrophobic substituents at the C17 position of EMATE [35,36]. Although a series of (p-sulphamoyl)-N-alkanoyl tyramines have also shown good inhibitory activities, the best compound in this series (N-tetradecanoyl) has been reported to be less potent than EMATE [35]. We demonstrate here, therefore, for the first time that superior inhibition over EMATE can be achieved with an inhibitor that is essentially non-steroidal by nature.

Although the coumarin moiety of 17 is expected to mimic the A/B-ring of EMATE, its third ring could not be described as a close mimic of the C/D-ring of EMATE when its preferred conformation is examined. Our molecular modelling of 17 (Graphics 1) shows that its 7-membered ring is largely in the chair form, which is similar to that of cycloheptene [50], with the C=C moiety taking the place of one of the ring carbon atoms in the cyclohexane chair. Despite this lack of absolute conformational resemblance of 17 to EMATE, particularly in the C/D ring regions, the hydrophobic interactions between its cycloalkene system and neighbouring amino acid residues in the enzyme active site must be effective and favourable. As a consequence, the active site sulphamoylation, and hence inactivation, of E1-STS by 17, must be facilitated. For 20, despite a higher hydrophobicity by virtue of an extra methylene group, its lower potency than 17 observed could be attributed to the highly strained multi-conformational cyclooctene system. It is possible that the binding conformation of the cyclooctene system of 20 might have less optimal interactions with the amino acid residues of the enzyme active site than the cycloheptene system of 17.

We have demonstrated previously that 7-(sulphooxy)-4-methylcoumarin is a substrate for E1-STS [28]. However, it is important to demonstrate the same with 667COUMARIN sulphate (18, Scheme 2B), which we synthesised by treating a solution of 16 (Scheme 2) in sodium hydroxide (~1M) with sulphur trioxide-trimethylamine complex. When 18 was incubated with placental microsomes in the absence of EMATE (see Materials and Methods), only the free coumarin 16 was detected. However, hydrolysis of 18 by E1-STS was completely abolished by the inclusion of EMATE in the reaction (data not shown). These results therefore indicate that the tricyclic coumarin sulphate, 18 is a substrate for this enzyme.

The oestrogenic activity of 17 was also studied. Like COUMATE [31], when administered orally, 17 was found to be devoid of oestrogenicity as shown by its ability to block completely the effect of E1S on stimulating uterine growth in ovariectomized rats (data not shown and will be reported elsewhere). With this lack of oestrogenicity, together with its higher active site-directed inhibitory activity against E1-STS than EMATE in vitro and also its ease of synthesis, 17 is now in formal pre-clinical development for Phase I Clinical Trial for the treatment of postmenopausal women with HDBC.

In a limited structure-activity relationship study for our tricyclic coumarin sulphamates, we enlarged the middle ring of 666COUMATE (15, Scheme 2) from the α,β-unsaturated δ-lactonic to the unconjugated ε-lactonic moiety of 22 (Scheme 2). It is clear that the potency of 15 was significantly reduced by such structural modification as shown by the weaker inhibitory activity of 22 (Table 2). This result is consistent with the findings from our recent structure-activity relationships study on COUMATE which have shown a similar detrimental effect to the potency of the parent compound when the conjugation of the coumarin ring is either disrupted or removed entirely [28]. Our explanation for this effect is that the breaking of the S—O—Ar bond in the sulphamate group of coumarin sulphamates such as COUMATE during sulphamoylation of E1-STS is assisted by the extended conjugation present in the coumarin motif. Such conjugation improves the leaving group ability of coumarins by lowering the pKa of the phenol (Our recent finding that the 4-nitro analogue of EMATE is more potent than EMATE as a steroid sulphatase inhibitor [51] has already suggested that the inhibitory activity of an aryl sulphamate could be improved by enhancing the leaving group ability of the parent phenol, i.e. lowering of pKa). Any disruption or removal of conjugation in the ring system of coumarins, including that in 14, should therefore render analogues with poorer leaving group abilities (i.e. a higher pKa value for the parent phenol) whose sulphamates are expected to be less active as E1-STS inhibitors. However, the susceptibility of the unconjugated β,γ-unsaturated ε-lactonic moiety of 22 to hydrolysis in phosphate buffered saline (pH=7.4) used in the bioassay could explain the relatively weak inhibition shown by this inhibitor. It is possible that the tricyclic structure of 22, supposedly required for good inhibitory activity, is already lost prior to the binding of the inhibitor to the enzyme active site.

Materials and Methods

Materials

All chemicals were either purchased from Aldrich Chemical Co. (Gillingham, Dorset, U.K.) or Lancaster Synthesis (Morecambe, Lancashire, U.K. All organic solvents, of A.R. grade, were supplied by Fison plc (Loughborough, U.K.) and stored over 4 Å molecular sieves. Anhydrous dimethylformamide (DMF), used for all the sulphamoylation reactions, was purchased from Aldrich and was stored under a positive pressure of $N_2$ after use. Sulphamoyl chloride was prepared by an adaptation of the method of Appel and Berger [66] and was stored as a solution in toluene as described by Woo et. al. [28,37]. An appropriate volume of this solution was freshly concentrated in vacuo immediately before use.

E1S and E1 were purchased from Sigma Chemical Co. (Poole, U.K.). [6,7-$^3$H]-E1S (specific activity, 50 Ci/mmol) and [4-$^{14}$C]-E1 (specific activity, 52 mCi/mmol) were purchased from New England Nuclear (Boston, Mass.). [6,7-$^3$H]-E1 (specific activity, 97 Ci/mmol) was obtained from the Amersham International Radiochemical Centre (Amersham, U.K.).

Thin Layer Chromatography (TLC) was performed on pre-coated plates (Merck TLC aluminium sheets silica gel 60 $F_{254}$, Art. No. 5554). Product(s) and starting material (SM) were detected by viewing under UV light (all parent coumarins also give an intense purple fluorescence at 366 nm) and/or treating with a methanolic solution of phosphomolybdic acid followed by heating. Preparative TLC was performed on precoated plates (Merck TLC silica gel 60 $F_{254}$, 20×20 cm, layer thickness 2 mm, art. no. 5717) and bands were visualised under UV light. Flash column chromatography was performed on silica gel (Sorbsil C60). IR spectra were determined by a Perkin-Elmer 782 infrared spectrophotometer, and peak positions are expressed in $cm^{-1}$. $^1$H and DEPT edited $^{13}$C NMR spectra of compounds were recorded with a Jeol JMN-GX270 and JMN-GX400 NMR spectrometers, and chemical shifts are reported in parts per million (ppm, δ) relative to tetramethylsilane (TMS) as an internal standard. FAB-mass spectra were recorded at the Mass Spectrometry Service Centre, University of Bath, using m-nitrobenzyl alcohol (NBA) as the matrix. Elemental analyses were performed by the Microanalysis Service, University of Bath. Melting points were determined using a Reichert-Jung Thermo Galen Kofler block and are uncorrected.

Biological studies were performed essentially as described previously [24,25,67]. For more details, see legends of individual Figures or Tables. To examine whether the sodium salt of 6-oxo-3-sulfooxy-8,9,10,11-tetrahydro-7H-cyclohepta-[c][1]benzopyran (18, Scheme 2) could act as a substrate for E1-STS, 100 μg of the compound was incubated for 1 h with placental microsomes in the absence or presence of EMATE (10 μM). The product formed at the end of the incubation was extracted into diethyl ether. After evaporation of solvent, the residue obtained was examined by TLC using ether/methanol (2:1) as eluent. In this mobile phase, the tricyclic sulphate, 18 and the parent 3-hydroxy-6-oxo-8,9,10,11-tetrahydro-7H-cyclohepta-[c][1]benzopyran (16, Scheme 2) have $R_f$ values of 0.6 and 0.86 respectively.

pKa Determination of 667COUMATE

A 5 mM solution of 667COUMATE (17) in water/methanol (1:1) at room temperature was prepared and its pH read (WPA Linton Cambridge UK, CCMD625 pH meter). The titrant (50 mM KOH) was then added in equal portions. The pH was recorded after each addition when equilibrium has been reached (after stirring). The titration was completed within 10 min after the first addition of titrant. The pKa was determined according to the procedure of Albert and Serjeant [61].

Synthesis

4-Ethyl-7-hydroxycoumarin (3)

Resorcinol (1.21 g, 11.0 mmol) was dissolved in hot ethyl propionylacetate (1.52 g, 10.0 mmol). To this stirred mixture at ice-water temperature was added dropwise a mixture of trifluoroacetic acid (1.70 mL, 22.0 mmol) and concentrated sulphuric acid (2.2 mL, 22.0 mmol) at such a rate that the reaction temperature was kept below 10° C. (about 30 min). The reaction mixture was then allowed to warm to room temperature and thereupon stirred for an additional 3 h before being quenched cautiously with ice-water. After stirring the suspension that formed for 1 h, the bright yellow precipitate was collected by suction filtration, washed exhaustively with water and then re-dissolved into acetone. The resulting solution was heated with activated charcoal, filtered and evaporated to give a light orange residue which was dried azeotropically with isopropyl alcohol. The crude product that obtained was purified by recrystallisation from acetone/hexane (2:3) to give 3 as creamy crystals (806 mg, 4.24 mmol, 42%); mp 175–178° C. [Lit. [68] 177° C. (ethanol)]; $\delta_H$ (400 MHz, DMSO-$d_6$) 1.22 (3H, t, J=7.3 Hz, $CH_3$), 2.77 (2H, q, J=7.3 Hz, $CH_2$), 6.09 (1H, s, C3-H), 6.71 (1H, d, $J_{C6-H, C8-H}$=2.4 Hz, C8-H), 6.80 (1H, dd, $J_{C8-H, C6-H}$=2.4 Hz and $J_{C6-H, C6-H}$=8.4 Hz, C6-H), 7.64 (1H, d, $J_{C6-H, C5-H}$=8.8 Hz, C5-H) and 10.53 (1H, s, exchanged with $D_2O$, OH); MS (FAB+) m/z (rel. intensity) 190.8[100, (M+H)$^+$]; MS (FAB−) m/z (rel. intensity) 342.8[60, (M−H+NBA)$^-$], 188.8[100, (M−H)$^-$]. Found: C, 69.4; H, 5.35; $C_{11}H_{10}O_3$ requires C, 69.43; H, 5.30%.

4-Ethylcoumarin-7-O-sulphamate (4)

To a stirred solution of 3 (400 mg, 1.96 mmol) in anhydrous DMF (5 mL) at 0° C. under an atmosphere of $N_2$ was added sodium hydride (60% dispersion, 78 mg, 1.96 mmol) followed by sulfamoyl chloride (3 eq.) after the evolution of hydrogen had ceased. The reaction mixture was stirred under $N_2$ at room temperature overnight and then poured into water (150 mL). The resulting mixture was extracted with ethyl acetate (150 mL) and the organic portion separated was washed with brine (5×100 mL), dried ($MgSO_4$), filtered and evaporated in vacuo at 40° C. The crude product that obtained was recrystallised from ethyl acetate/hexane (1:1) to give 4 as white crystals (278 mg, 1.03 mmol, 49%); mp 168–169° C.; $\delta_H$ (400 MHz, DMSO-$d_6$) 1.25 (3H, t, J=7.3 Hz, $CH_3$), 2.85 (2H, q, J=7.3 Hz, $CH_2$), 6.37 (1H, s, C3-H), 7.29 (1H, dd, $J_{C8-H, C6-H}$=2.4 Hz and $J_{C5-H, C6-H}$=8.8 Hz, C6-H), 7.33 (1H, d, $J_{C6-H, C8-H}$=2.4 Hz, C8-H), 7.93 (1H, d, $J_{C6-H, C5-H}$=8.8 Hz, C5-H) and 8.24 (2H, s, exchanged with $D_2O$, $OSO_2NH_2$); MS (FAB+) m/z (rel. intensity) 270.1[100, (M+H)$^+$], 191.1[10, (M+H—$HNSO_2$)$^+$]; MS (FAB−) m/z (rel. intensity) 422.1[15, (M+NBA)$^-$], 268.0[100, (M−H)$^-$], 189.1[35, (M−$H_2NSO_2$)$^-$]; HRMS (FAB+) m/z 270.04448 [(M+H)$^+$], calcd for $C_{11}H_{12}NO_5S$ 270.04362. Found: C, 48.9; H, 4.06; N, 5.04; $C_{11}H_{11}NO_5S$ requires C, 49.06; H, 4.12; N, 5.20%.

7-Hydroxy-4-(n-propyl)coumarin (5)

This was prepared from ethyl butyrylacetate (1.61 g, 10.0 mmol) in a similar manner to the preparation of 3. The crude product that obtained was purified by recrystallisation from acetone/hexane (1:2) to give 5 as light yellow crystals (a total of 1.26 g, 6.17 mmol, 62%); mp 135–137° C. (Lit. [69] 130° C. (ethanol)]; $\delta_H$ (400. MHz, DMSO-$d_6$) 0.97 (3H, t, J=7.5 Hz, $CH_3$), 1.63 (2H, sextet, J=7.5 Hz, —$CH_2CH_2CH_3$), 2.71 (2H, t, J=7.6 Hz, —$CH_2CH_2CH_3$), 6.08 (1H, s, C3-H), 6.71 (1H, d, J=2.4 Hz, C8-H), 6.80 (1H, dd, J=2.4 and 8.4 Hz, C6-H), 7.65 (1H, d, J=8.5 Hz, C5-H) and 10.53 (1H, s, exchanged with $D_2O$, OH); MS (FAB+) m/z (rel. intensity) 408.7[15, (2M)$^+$], 204.8[100, (M+H)$^+$]; MS (FAB−) m/z (rel. intensity) 406.8[20, (2M−H)$^-$], 356.8[20, (M−H+NBA)$^-$], 202.8[100, (M−H)$^-$]. Found: C, 70.5; H, 6.00; $C_{12}H_{12}O_3$ requires C, 70.56; H, 5.93%.

4-(n-Propyl)coumarin-7-O-sulphamate (6)

This was prepared from 5 (400 mg, 1.96 mmol) in a similar manner to the preparation of 4. The crude product that obtained was purified by recrystallisation from ethyl acetate/hexane (1:1) to give 6 as white 'cotton-like' crystals (242 mg, 854 μmol, 44%); mp 174–178° C.; TLC (chloroform/ethyl acetate, 2:1) $R_f$ 0.32, c.f. $R_f$ 0.41 (5); $\delta_H$ (270 MHz, DMSO-$d_6$) 0.99 (3H, t, J=7.4 Hz, $CH_3$), 1.66 (2H, sextet, J=7.5 Hz, —$CH_2CH_2CH_3$), 2.80 (2H, t, J=7.5 Hz, —$CH_2CH_2CH_3$), 6.38 (1H, s, C3-H), 7.29 (1H, dd, J=2.4 and 8.6 Hz, C6-H), 7.33 (1H, d, J=2.4 Hz, C8-H), 7.95 (1H, d, J=8.6 Hz, C5-H) and 8.25 (2H, s, exchanged with $D_2O$, $OSO_2NH_2$); MS (FAB+) m/z (rel. intensity) 284.1[100, (M+H)$^+$], 205.2[8, (M+H—$HNSO_2$)$^+$]; MS (FAB−) m/z (rel. intensity) 436.1[15, (M−H+NBA)$^-$], 282.1[100, (M−H)$^-$], 203.1[36, (M−$H_2NSO_2$)$^-$]; HRMS (FAB+) m/z 284.05950 [(M+H)$^+$], calcd for $C_{12}H_{14}NO_5S$ 284.05927. Found: C, 50.8; H, 4.64; N, 4.81; $C_{12}H_{13}NO_5S$ requires C, 50.87; H, 4.63; N, 4.95%.

3-Ethyl-7-hydroxyl-4-methylcoumarin (7)

This was prepared from ethyl 2-ethylacetoacetate (1.63 g, 10.0 mmol) in a similar manner to the preparation of 3. The crude product that obtained was purified by recrystallisation from isopropyl alcohol/hexane (3:5) to give 7 as white crystals (a total of 1.24 g, 6.07 mmol, 61%); mp 201–203° C. (Lit. [70] 196–197° C.); $\delta_H$ (400 MHz, DMSO-$d_6$) 1.03 (3H, t, J=7.5 Hz, $CH_3$), 2.36 (3H, s, C4-$CH_3$), 2.54 (2H, q, J=7.3 Hz, $CH_2$), 6.68 (1H, d, J=2.4 Hz, C8-H), 6.79 (1H, dd, J=2.4 and 8.4 Hz, C6-H), 7.60 (1H, d, J=8.8 Hz, C5-H) and 10.38 (1H, br s, exchanged with $D_2O$, OH); MS (FAB+) m/z (rel. intensity) 409.2[10, (2M+H)$^+$], 205.2[100, (M+H)$^+$]; MS (FAB−) m/z (rel. intensity) 407.2[16, (2M−H)$^-$], 357.2 [36, (M+NBA)$^-$], 203.2[100, (M−H)$^-$]; HRMS (FAB+) m/z 205.08669 [(M+H)$^+$], calcd for $C_{12}H_{13}O_3$ 205.08647. Found: C, 70.2; H, 5.93; $C_{12}H_{12}O_3$ requires C, 70.56; H, 5.93%.

3-Ethyl-4-methylcoumarin-7-O-sulphamate (8)

This was prepared from 7 (400 mg, 1.96 mmol) in a similar manner to the preparation of 4. The crude product that obtained was purified by recrystallisation from ethyl acetate/hexane (1:1) to give 8 as white crystals (204 mg, 720 µmol, 37%); mp 179–181° C.; $\delta_H$ (270 MHz, DMSO-d$_6$) 1.06 (3H, t, J=7.5 Hz, CH$_3$), 2.44 (3H, s, C4-CH$_3$), 2.61 (2H, q, J=7.5 Hz, CH$_2$), 7.28 (2H, m, C6-H and C8-H), 7.89 (1H, d, J=8.4 Hz, C5-H) and 8.21 (2H, br s, exchanged with D$_2$O, OSO$_2$NH$_2$); MS (FAB+) m/z (rel. intensity) 284.1[100, (M+H)$^+$], 205.1[14, (M+H—HNSO$_2$)$^+$]; MS (FAB–) m/z (rel. intensity) 436.1[12, (M–H+NBA)$^-$], 282.1[100, (M–H)$^-$], 203.1[28, (M–H$_2$NSO$_2$)$^-$]; HRMS (FAB+) m/z 284.05984 [(M+H)$^+$], calcd for $C_{12}H_{14}NO_5S$ 284.05927. Found: C, 50.9; H, 4.67; N, 4.80; $C_{12}H_{13}NO_5S$ requires C, 50.87; H, 4.63; N, 4.95%.

Ethyl 2-(n-propyl)acetoacetate (9)

Keto ester 9 was synthesized according to the method of Barbry et. al. [71]. A mixture of potassium carbonate (14 g, 0.10 mol), ethyl acetoacetate (4.3 g, 33 mmol), 1-iodopropane (5.7 g, 33.7 mmol), tetrabutylammonium chloride hydrate (10 g), water (50 mL) and chloroform (50 mL) was stirred at room temperature for 40 h. The aqueous layer was then separated, acidified with 5M hydrochloric acid and extracted with ether. The organic portions were combined, concentrated and the residual tetrabutylammonium chloride was precipitated by addition of ether. After filtration, the ethereal filtrate was dried (MgSO$_4$) and evaporated to give a yellow liquid which was fractionated by distillation. The fraction which boiled at 93° C. at ~15 mmHg (Lit. [72] 106–107° C., 22 mmHg) was collected (2.13 g) and $^1$H NMR has indicated that this colourless liquid contained about 5% of ethyl acetoacetate and 95% of 9; $\delta_H$ (270 MHz, CDCl$_3$) 0.93 (3H, t, J=7.3 Hz, CH$_3$), 1.28 (5H, m, —CH$_2$CH$_2$CH$_3$ and CH$_3$), 1.83 (2H, m, —CH$_2$CH$_2$CH$_3$), 2.23 (3H, s, CH$_3$CO), 3.42 (1H, t, J=7.3 Hz, —CH) and 4.20 (2H, q, J=7.3 Hz, COOCH$_2$CH$_3$); MS (EI) m/z (rel. intensity) 172.1(25, M$^+$), 143.1[50, (M–Et)$^+$], 130.1[28, (M+H—CH$_3$CO)$^+$], 115.1(23), 101.1(40), 85.0(20), 69.0(30), 55.0 (30), 43.0[100, (CH$_3$CO)$^+$]. This crude 9 was used for the next reaction without further purification.

7-Hydroxy-4-methyl-3-(n-propyl)coumarin (10)

This was prepared from 9 (1.72 g) in a similar manner to the preparation of 3. The yellow/brown crude product that obtained was fractionated by flash chromatography (chloroform/acetone, 20:1 to 1:1 gradient). The product that isolated was further purified by recrystallisation from ethyl acetate/hexane (2:3) to give 10 as creamy crystals (813 mg, 3.73 mmol, ca. 37%); mp 160–173° C. [Lit. [73] 171–173° C. (aq. ethanol)]; $\delta_H$ (400 MHz, DMSO-d$_6$) 0.92 (3H, t, J=7.3 Hz, CH$_3$), 1.45 (2H, sextet, J=7.5 Hz, —CH$_2$CH$_2$CH$_3$), 2.36 (3H, s, C4-CH$_3$), 2.51 (2H, t, J=7.7 Hz, —CH$_2$CH$_2$CH$_3$), 6.67 (1H, d, J=2.4 Hz, C8-H), 6.79 (1H, dd, J=2.4 and 8.4 Hz, C6-H), 7.60 (1H, d, J=8.8 Hz, C5-H) and 10.38 (1H, br s, exchanged with D$_2$O, OH); MS (FAB+) m/z (rel. intensity) 437.2[10, (2M+H)$^+$], 219.2[100, (M+H)$^+$]; MS (FAB–) m/z (rel. intensity) 435.2[12, (2M–H)$^-$], 371.1 [15, (M+NBA)$^-$], 217.1[100, (M–H)$^-$]; HRMS (FAB+) m/z 219.10300 [(M+H)$^+$], calcd for $C_{13}H_{15}O_3$ 219.10212. Found: C, 71.7; H, 6.49; $C_{13}H_{14}O_3$ requires C, 71.53; H, 6.47%.

4-Methyl-3-(n-propyl)coumarin-7-O-sulphamate (11)

This was prepared from 10 (300 mg, 1.38 mmol) in a similar manner to the preparation of 4. The grey syrupy crude product that obtained was fractionated by flash chromatography (chloroform/ethyl acetate, 20:1 to 1:1 gradient). The product that isolated was further purified by recrystallisation from ethyl acetate/hexane (1:3) to give 11 as white crystals (137 mg, 461 µmol, 34%); mp 139–142° C.; $\delta_H$ (270 MHz, DMSO-d$_6$) 0.93 (3H, t, J=7.3 Hz, CH$_3$), 1.48 (2H, m, —CH$_2$CH$_2$CH$_3$), 2.44 (3H, s, C4-CH$_3$), 2.58 (2H, t, J=7.5 Hz, —CH$_2$CH$_2$CH$_3$), 7.27 (2H, m, C6-H and C8-H), 7.89 (1H, d, J=8.4 Hz, C5-H) and 8.21 (2H, s, exchanged with D$_2$O, OSO$_2$NH$_2$); MS (FAB+) m/z (rel. intensity) 298.1 [100, (M+H)$^+$]; MS (FAB–) m/z (rel. intensity) 593.2[25, (2M–H)$^-$], 296.1[100, (M–H)$^-$], 217.1[45, (M–HNSO$_2$)$^-$]; HRMS (FAB+) m/z 298.07332 [(M+H)$^+$], calcd for $C_{13}H_{16}NO_5S$ 298.07492. Found: C, 52.4; H, 5.08; N, 4.67; $C_{13}H_{15}NO_5S$ requires C, 52.51; H, 5.09; N, 4.71%.

7-Hydroxy-4-oxo-2,3-dihydro-1H-cyclopenta-[c][1]benzopyran (12)

This was prepared from methyl 2-oxocyclopentane carboxylate (1.47 g, 10.0 mmol) in a similar manner to the preparation of 3. The crude product that obtained was purified by recrystallisation from isopropyl alcohol/hexane (1:1) to give 12 as pale pink/white crystals (1.40 g, 6.92 mmol, 69%); mp 248–251° C. [Lit. [74] 243.5° C. (aq. ethanol)]; $\delta_H$ (270 MHz, DMSO-d$_6$) 2.09 (2H, quintet, J~7.6 Hz, C2-H$_2$), 2.71 (2H, t, J~7.3 Hz, C3-H$_2$), 3.02 (2H, t, J~7.7 Hz, C1-H$_2$), 6.74 (1H, d, $J_{C8-H, C6-H}$=2.2 Hz, C6-H), 6.79 (1H, dd, $J_{C6-H, C8-H}$=2.2 Hz and $J_{C9-H, C8-H}$~8.4 Hz, C8-H), 7.43 (1H, d, $J_{C8-H, C9-H}$~8.4 Hz, C9-H) and 10.43 (1H, br s, exchanged with D$_2$O, OH); MS (FAB+) m/z (rel. intensity) 203.2[100, (M+H)$^+$]; MS (FAB–) m/z (rel. intensity) 355.2 [36, (M+NBA)$^-$], 201.1[100, (M–H)$^-$]. Found: C, 71.0; H, 4.90; $C_{12}H_{10}O_3$ requires C, 71.26; H, 4.99%.

4-Oxo-2,3-dihydro-1H-cyclopenta-[c][1]benzopyran-7-O-sulphamate (13)

This was prepared from 12 (500 mg, 2.47 mmol) in a similar manner to the preparation of 4. The crude product that obtained was purified by recrystallisation from acetone/hexane (3:5) to give 13 as white crystals (403 mg, 1.43 mmol, 58%); mp 193–195° C.; $\delta_H$ (400 MHz, acetone-d$_6$) 2.22 (2H, quintet, J~7.6 Hz, C2-H$_2$), 2.84 (2H, m, C3-H$_2$), 3.15 (2H, m, C1-H$_2$), 7.29 (1H, dd, $J_{C6-H, C8-H}$~2.2 Hz and $J_{C9-H, C8-H}$=8.7 Hz, C8-H), 7.33 (1H, d, $J_{C8-H, C6-H}$=2.1 Hz, C6-H), 7.35 (2H, br s, exchanged with D$_2$O, OSO$_2$NH$_2$) and 7.67 (1H, d, $J_{C8-H, C9-H}$=8.2 Hz, C9-H); MS (FAB+) m/z (rel. intensity) 282.0[100, (M+H)$^+$], 202.1[10, (M–HNSO$_2$)$^+$]; MS (FAB–) m/z (rel. intensity) 434.1[22, (M+NBA)$^-$], 280.1[100, (M–H)$^-$], 201.1[26, (M–H$_2$NSO$_2$)$^-$]; HRMS (FAB+) m/z 282.04493 [(M+H)+], calcd for $C_{12}H_{12}NO_5S$ 282.04362. Found: C, 51.3; H, 3.84; N, 4.90; $C_{12}H_{11}NO_5S$ requires C, 51.24; H, 3.94; 4.98%.

3-Hydroxy-6-oxo-7,8,9,10-tetrahydro-dibenzo[b,d]pyran (14)

This was prepared from ethyl 2-cyclohexanone carboxylate (1.79 g, 10.0 mmol) in a similar manner to the preparation of 3. The crude product that obtained was purified by recrystallisation from isopropyl alcohol/hexane (3:2) to give 14 as creamy crystals (1.45 g, 6.71 mmol, 67%); mp 200–202° C. [Lit. [75] 203–204° C. (aq. ethanol)]; $\delta_H$ (270 MHz, DMSO-d$_6$) 1.74 (4H, m, C8-H$_2$ and C9-H$_2$), 2.38 (2H, m, C7-H$_2$), 2.74 (2H, m, C10-H$_2$), 6.69 (1H, d, $J_{C2-H, C4-H}$=2.2 Hz, C4-H), 6.78 (1H, dd, $J_{C4-H, C2-H}$=2.4 Hz and $J_{C1-H, C2-H}$=8.6 Hz, C2-H), 7.53 (1H, d, $J_{C2-H, C1-H}$=8.4

Hz, C1-H+) and 10.34 (1H, s, exchanged with D$_2$O, OH); $\delta_H$ (100.4 MHz, DMSO-d$_6$) 20.77 (t), 21.16 (t), 23.39 (t), 24.51 (t), 101.83 (d), 111.87 (s), 112.56 (d), 118.34 (s), 124.93 (d), 147.58 (s), 152.94 (s), 159.76 (s) and 160.90 (s); MS (FAB+) m/z (rel. intensity) 217.2[100, (M+H)+]; MS (FAB−) m/z (rel. intensity) 369.2[30, (M+NBA)−], 215.1[100, (M−H)−]. Found: C, 72.0; H, 5.60; C$_{13}$H$_{12}$O$_3$ requires C, 72.21; H, 5.59%. * An NOE interaction was observed between these two protons.

6-Oxo-7,8,9,10-tetrahydro-dibenzo[b,d]pyran-3-O-sulphamate (15)

This was prepared from 14 (300 mg, 1.39 mmol) in a similar manner to the preparation of 4. The crude product that obtained was purified by recrystallisation from acetone/hexane (1:2) to give 15 as white crystals (204 mg, 691 μmol, 50%); mp 184.5–186.5° C.; $\delta_H$ (270 MHz, acetone-d$_6$) 1.84 (4H, m, C8-H$_2$ and C9-H$_2$), 2.50 (2H, m, C7-H$_2$), 2.85 (2H, m, C10-H$_2$), 7.3 (4H, m, 2H exchanged with D$_2$O, C2-H, C4-H and OSO$_2$NH$_2$) and 7.78 (1H, d, J$_{C2-H, C1-H}$~8 Hz, C1-H); MS (FAB+) m/z (rel. intensity) 296.3[100, (M+H)+], 217.2[13, (M+H−HNSO$_2$)+]; MS (FAB−) m/z (rel. intensity) 448.1[14, (M+NBA)−], 294.1[100, (M−H)−], 215.1[28, (M−H$_2$NSO$_2$)−]; HRMS (FAB+) m/z 296.05921 [(M+H)+], calcd for C$_{13}$H$_{14}$NO$_5$S 296.05927. Found: C, 53.0; H, 4.50; N, 4.60; C$_{13}$H$_{13}$NO$_5$S requires C, 52.87; H, 4.44; N, 4.75%.

3-Hydroxy-6-oxo-8,9,10,11-tetrahydro-7H-cyclohepta-[c][1]benzopyran (16)

This was prepared from methyl 2-oxocycloheptane carboxylate (1.72 g, 10.0 mmol) in a similar manner to the preparation of 3. The crude product that obtained was purified by recrystallisation from ethyl acetate/hexane (7:4) to give 16 as creamy crystals (1.47 g, 6.38 mmol, 64%); mp 189–190° C. [Lit. [76] 188.5–189.5° C. (ethanol)]; $\delta_H$ (400 MHz, DMSO-d$_6$) 1.49 (2H, m), 1.58 (2H, m), 1.83 (2H, m), 2.76 (2H, m, C7-H$_2$), 2.93 (2H, m, C11-H$_2$), 6.70 (1H, d, J=2.4 Hz, C4-H), 6.78 (1H, dd, J=2.4 and 8.7 Hz, C2-H), 7.71 (1H, d, J=8.8 Hz, C1-H) and 10.41 (1H, br s, exchanged with D$_2$O, OH); MS (FAB+) m/z (rel. intensity) 461.2[13, (2M+H)+], 231.1[100, (M+H)+]; MS (FAB−) m/z (rel. intensity) 383.3[25, (M+NBA)−], 229.2[100, (M−H)−]. Found: C, 73.1; H, 6.16; C$_{14}$H$_{14}$O$_3$ requires C, 73.01; H, 6.13%.

6-Oxo-8,9,10,11-tetrahydro-7H-cyclohepta-[c][1]benzopyran-3-O-sulphamate (17)

This was prepared from 16 (400 mg, 1.74 mmol) in a similar manner to the preparation of 4. The crude product that obtained was fractionated by flash chromatography (chloroform/ethyl acetate, 8:1 to 2:1, gradient) and the product that isolated was further purified by recrystallisation from ethyl acetate/hexane (3:5) to give 17 as white crystals (310 mg, 1.00 mmol, 58%); mp 169–171° C.; TLC (chloroform/ethyl acetate, 4:1) R$_f$ 0.33, c.f. R$_f$ 0.52 (18); IR (KBr) 3310, 3060, 2930, 2860, 1690, 1610, 1390, 1190; $\delta_H$ (270 MHz, acetone-d$_6$) 1.61 (2H, m), 1.70 (2H, m), 1.94 (2H, m), 2.90 (2H, m, C7-H$_2$), 3.07 (2H, m, C11-H$_2$), 7.29 (2H, m, C2-H and C4-H), 7.36 (2H, br s, exchanged with D$_2$O, OSO$_2$NH$_2$) and 7.95 (1H, d, J~9 Hz, C1-H); MS (FAB+) m/z (rel. intensity) 310.1[100, (M+H)+], 230.1[10, (M−HNSO$_2$)+]; MS (FAB−) m/z (rel. intensity) 462.3[15, (M+NBA)−], 308.2[100, (M−H)−], 229.2[36, (M−H$_2$NSO$_2$)−]; HRMS (FAB+) m/z 310.07529. [(M+H)+], calcd for C$_{14}$H$_{16}$NO$_5$S 310.07492. Found: C, 54.35; H, 4.96; N, 4.53; C$_{14}$H$_{15}$NO$_5$S requires C, 54.36; H, 4.89; N, 4.53%.

6-Oxo-3-sulfooxy-8,9,10,11-tetrahydro-7H-cyclohepta-[c][1]benzopyran (18)

To a stirred solution of 16 (100 mg, 434 μmol) in sodium hydroxide (~1M, 1.5 mL) at room temperature was added sulphur trioxide-trimethylamine complex (126 mg, 868 μmol). After being stirred for 3 days, the reaction mixture was fractionated by flash chromatography (ether; then ether/methanol, 4:1 to 1:1, gradient) to give 18 as dull white residue (110 mg); TLC (ether/methanol, 2:1) R$_f$ 0.6, c.f. R$_f$ 0.86 (16 in~1M NaOH); $\delta_H$ (400 MHz, DMSO-d$_6$) 1.50 (2H, m), 1.60 (2H, m), 1.84 (2H, m), 2.79 (2H, m, C7-H$_2$), 2.98 (2H, m, C11-H$_2$), 7.15 (1H, dd, J=2.3 and 8.7 Hz, C2-H), 7.18 (1H, d, J=2.1 Hz, C4-H) and 7.81 (1H, d, J=8.8 Hz, C1-H); MS (FAB−) m/z (rel. intensity) 641.1[18, (2M−Na)−], 485.1[16, (M−H+NBA)−], 309.1[100, (M−Na)−], 229.1[26, (M−Na—SO$_3$)−]; HRMS (FAB−) m/z 309.04310 [(M−Na)+], calcd for C$_{14}$H$_{13}$O$_6$S 309.04329.

3-Hydroxy-6-oxo-7,8,9,10,11,12-hexahydro-cycloocta-[c][1]benzopyran (19)

This was prepared from methyl 2-oxocyclooctane carboxylate (1.02 g, 5.0 mmol) and resorcinol (610 mg, 5.5 mmol) in a similar manner to the preparation of 3. After quenching the reaction mixture with ice-water, the crude product was extracted into ethyl acetate (150 ml). The organic portion which separated was then further washed with brine (5×100 ml), dried (MgSO$_4$), filtered and evaporated. The orange liquid/solid obtained was then fractionated by flash chromatography (ethyl acetate/hexane, 1:4 to 2:1 gradient) and 19 that isolated (405 mg, 1.66 mmol, 33%) was recrystallised from ethyl acetate/hexane (5:2) to give fine white crystals (256 mg); TLC (ethyl acetate/hexane, 1:1) R$_f$ 0.42, c.f. R$_f$>0.7 (keto ester); mp 232–234° C.; $\delta_H$ (400 MHz, DMSO-d$_6$) 1.38 (2H, m), 1.49 (2H, m), 1.60 (2H, m), 1.74 (2H, m), 2.71 (2H, t, J~5.6 Hz, C7-H$_2$), 2.99 (2H, t, J~6.3 Hz, C12-H$_2$), 6.72 (1H, d, J=2.4 Hz, C4-H), 6.81 (1H, dd, J=2.3 and 8.7 Hz, C2-H), 7.66 (1H, d, J=8.8 Hz, C1-H) and 10.42 (1H, br s, exchanged with D$_2$O, OH); MS (FAB+) m/z (rel. intensity) 245.1[100, (M+H)+]; MS (FAB−) m/z (rel. intensity) 397.3[30, (M+NBA)−], 243.2 [100, (M−H)−]. Found: C, 73.6; H, 6.67; C$_{15}$H$_{16}$O$_3$ requires C, 73.74; H, 6.61%. About 500 mg of the starting keto ester was retrieved.

6-Oxo-7,8,9,10,11,12-hexahydro-cycloocta-[c][1]benzopyran-3-O-sulphamate (20)

This was prepared from 19 (421 mg, 1.72 mmol) in a similar manner to the preparation of 4. The crude product that obtained was fractionated by flash chromatography (chloroform/ethyl acetate, 8:1 to 4:1, gradient) and the product that isolated was further purified by recrystallisation from ethyl acetate/hexane (1:2) to give 20 as white crystals (305 mg, 943 μmol, 55%); mp 174–175.5° C.; $\delta_H$ (270 MHz, acetone-d$_6$) 1.47 (2H, m), 1.55 (2H, m), 1.68 (2H, m), 1.86 (2H, m), 2.84 (2H, t, J~6.5 Hz, C7-H$_2$), 3.10 (2H, t, J~6.5 Hz, C12-H$_2$), 7.28 (2H, m, C2-H and C4-H), 7.37 (2H, br s, exchanged with D$_2$O, OSO$_2$NH$_2$) and 7.93 (1H, d, J~9 Hz, C1-H); MS (FAB+) m/z (rel. intensity) 324.1[100, (M+H)+], 244.1[13, (M−HNSO$_2$)+]; MS (FAB−) m/z (rel. intensity) 476.3[64, (M+NBA)−], 323.2[58, M−], 243.3[100, (M−H$_2$NSO$_2$)−]; HRMS (FAB+) m/z 324.08971 [(M+H)+], calcd for C$_{15}$H$_{18}$NO$_5$S 324.09057. Found: C, 55.8; H, 5.39; N, 4.39; C$_{15}$H$_{17}$NO$_5$S requires C, 55.71; H, 5.30; N, 4.33%.

3-Hydroxy-6-oxo-6,7,8,9,10,11-hexahydrodibenz[b,d]oxepin (21)

This was prepared from ethyl(2-oxocyclohexyl)acetate (1.90 g, 10.0 mmol) in a similar manner to the preparation of 3. The brown crude product that obtained was fractionated by flash chromatography to give 21 as a creamy residue (439 mg, 1.91 mmol, 19%); TLC (chloroform/ethyl acetate, 4:1) $R_f$ 0.46, c.f. 0.19 (resorcinol); MS (FAB+) m/z (rel. intensity) 461.3[12, $(2M+H)^+$], 230.1(100, M+); MS (FAB−) m/z (rel. intensity) 383.2[40, $(M-H+NBA)^-$], 229.2 [100, $(M-H)^-$]; HRMS (FAB+) m/z 230.09451 (M)$^+$, calcd for $C_{14}H_{14}O_3$ 230.09429. The $^1$H NMR spectrum of 21 in $CDCl_3$ agrees with that reported by Hua et. al. [77]. The phenolic 21 was sulphamoylated without further purification.

6-Oxo-6,7,8,9,10,11-hexahydrodibenz[b,d]oxepin-3-O-sulphamate (22)

This was prepared from 21 (389 mg, 1.69 mmol) in a similar manner to the preparation of 4. The brown syrup that obtained was fractionated by flash chromatography (chloroform/ethyl acetate, 8:1 to 2:1, gradient) and the product that isolated was further purified by recrystallisation from ethyl acetate/hexane (1:1) to give 22 as white crystals (186 mg, 601 μmol, 36%); mp 183–186° C.; $\delta_H$ (400 MHz, acetone-$d_6$) 1.76 (4H, m, C9-$H_2$ and C10-$H_2$), 2.35 (2H, br s, $CH_2$), 2.53 (2H, v br s, $CH_2$), 2.85 (2H, s, C7-$H_2$), 7.17 (1H, d, J=2.4 Hz, C4H), 7.24 (3H, reduced to 1H upon exchange with $D_2O$, dd, J=2.6 and 8.7 Hz, C2-H and $OSO_2NH_2$) and 7.65 (1H, d, J=8.8 Hz, C1-H). Found: C, 54.5; H, 4.97; N, 4.54; $C_{14}H_{15}NO_5S$ requires C, 54.36; H, 4.89; N, 4.53%.

N-(2,2-Diphenylethyl)sulphamide (25)

To a stirred solution of 4-(n-propyl)coumarin-7-O-sulphamate (6) (100 mg, 353 μmol) in anhydrous acetonitrile under nitrogen at room temperature was added 2,2-diphenylethylamine (4 equiv.) and the progress of the reaction was monitored by TLC (products were detected by treating with a methanolic solution of phosphomolybdic acid followed by heating). The disappearance of 6 was completed after 48 h with the formation of 7-hydroxycoumarin-4-(n-propyl)coumarin (5) and sulphamide 25. Upon evaporation of the reaction mixture in vacuo, the light yellow syrup that resulted in ethyl acetate (50 mL) was washed with dilute hydrochloric acid (2×30 mL) and then water to neutral. The organic layer was left to evaporate in the fume cupboard and the creamy residue that obtained was fractionated on preparative TLC eluted with chloroform/acetone (4:1) to give sulphamide 25 ($R_f$ 0.41, c.f. $R_f$ 0.56 for 5) as creamy residue (52 mg, 188 μmol, 53%); IR (KBr) 3360, 3260, 1430, 1350, 1160 cm$^{-1}$; $\delta_H$ (270 MHz, DMSO-$d_6$) 3.50 (2H, t, J~7 Hz, $CH_2NH$), 4.22 (1H, t, J~7–8 Hz, CH), 6.47 (1H, t, J~5 Hz, exchanged with $D_2O$, NH), 6.57 (2H, s, exchanged with $D_2O$, $SO_2NH_2$) and 7.2–7.4 (10H, m, Ar); MS (FAB+) m/z (rel. intensity) 277.1[100, $(M+H)^+$], 181.1[97, $(M+H-H_2NSO_2NH_2)^+$], 97.1[52, $(H_3NSO_2NH_2)^+$]; MS (FAB−) m/z (rel. intensity) 429.2[65, $(M+NBA)^-$], 275.2[100, $(M-H)^-$], 95.0[38, $HNSO_2NH_2)^-$]; HRMS (FAB+) m/z 277.10133 [$(M+H)^+$], calcd for $C_{14}H_{17}N_2O_2S$ 277.10108.

Sulphamic Acid and Imidazole Salt (26)

The reaction was carried out in a similar manner to 25 except that imidazole (4 equiv.) was used. White precipitate was detected after the reaction mixture was being stirred for 17 h and the disappearance of coumarin sulphamate 6 was completed after 4 days. The white precipitate formed was filtered, washed several times with fresh acetonitrile and air-dried to give salt 26 as white residue (43 mg, 261 μmol, 70%); m.p. 152–154° C.; IR (KBr) 3300, 3240, 3150, 3000, 2860, 1590 cm$^{-1}$; $\delta_H$ (400 MHz, DMSO-$d_6$) 7.40 (2H, s) and 8.45 (1H, s); MS (FAB+) m/z (rel. intensity) 375.2[18, (imidazole+H+2NBA)$^+$], 222.1[100, (imidazole+H+NBA)$^+$], 69.0[16, (imidazole+H)$^+$]; MS (FAB−) m/z (rel. intensity) 402.0[35, $(H_2NSO_2O+2NBA)^-$], 249.0[100, $(H_2NSO_2O+NBA)^-$], 95.9[65, $H_2NSO_2O^-$]. Found: C, 22.0; H, 4.29; N, 25.2; $C_3H_7N_3O_3S$ requires C, 21.82; H, 4.27; N, 25.44%. The melting point, the IR and MS spectra of 26 were comparable to those of the white solid (m.p. 148–154° C.) precipitated upon addition of a solution of sulphamic acid in DMF dropwise to a solution of imidazole in acetonitrile.

APPENDIX I REFERENCES

1. Castiglione-Gertsch, M. (1996). New aromatase inhibitors: more selectivity, less toxicity, unfortunately, the same activity. *Eur. J. Cancer*, 32A, 393–395.
2. Miller, W. R. (1996). Aromatase inhibitors—Where are we now? *Brit. J. Cancer*, 73, 415–417.
3. Santner, S. J., Feil, P. D., and Santen, R. J. (1984). In situ estrogen production via the estrone sulfatase pathway in breast tumors: relative importance vs. the aromatase pathway. *J. Clin. Endocrinol. Metab.* 59, 29–33.
4. Yamamoto, T., Kitawaki, J., Urabe, M., Honjo, H., Tamura, T., Noguchi, T., Okada, H., Sasaki, H., Tada, A., Terashima, Y., Nakamura, J., and Yoshihama, M. (1993). Estrogen productivity of endometrium and endometrial cancer tissue—influence of aromatase on proliferation of endometrial cancer cells. *J. Steroid Biochem. Molec. Biol.* 44, 463–468.
5. Noel, C. T., Reed, M. J., Jacobs, H. S., and James, V. H. T. (1981). The plasma concentration of oestrone sulphate in postmenopausal women: lack of diurnal variation, effect of ovariectomy, age and weight. *J. Steroid Biochem. Molec. Biol.* 14, 1101–1105.
6. James, V. H. T., McNeill, J. M., Lai, L. C., Newton, C. J., Ghilchik, M. W., and Reed, M. J. (1987). Aromatase activity in normal breast and breast tumor tissues: in vivo and in vitro studies. *Steroids*, 50, 269–279.
7. Tseng, L., Mazella, J., Lee, L. U., and Stone, M. L. (1983). Oestrogen sulphatase and oestrogen sulphotransferase in human primary mammary carcinoma. *J. Steroid Biochem.* 19, 1413–1417.
8. Naitoh, K., Honjo, H., Yamamoto, T., Urabe, M., Ogino, Y., Yasumura, T., and Nambara, T. (1989). Oestrone sulphate amd sulphatase activity in human breast cancer and endometrial cancer. *J. Steroid Biochem.* 33, 1049–1054.
9. Chetrite, G. S., Cortes-Prieto, J., Philippe, J. C., Wright, F., and Pasqualini, J. R. (2000). Comparison of estrogen concentrations, estrone sulfatase and aromatase activities in normal, and in cancerous, human breast tissues. *J. Steroid Biochem. Molec. Biol.* 72, 23–27.
10. Adams, J. B., Garcia, M., and Rochefort, H. (1981). Estrogenic effects of physiological concentrations of 5-androstene-3α,17β-diol and its metabolism in MCF-7 human breast cancer cells. *Cancer Res.* 41, 4720–4726.
11. Dauvois, S. and Labrie, F. (1989). Androstenedione and androst-5-ene-3α,17β-diol stimulate DMBA-induced mammary tumours—role of aromatase. *Breast Cancer Res. Treat.* 13, 61–69.
12. Labrie, F., Bélanger, A., Simard, J., Luu-The, V., and Labrie, C. (1995). DHEA and peripheral androgen and estrogen formation: intracrinology. *Ann. N.Y. Acad. Sci.* 774, 16–28.
13. Labrie, F. (1991). Intracrinology. *Mol. Cell. Endocrinol.* 78, C113–C118.
14. Poortman, J., Andriesse, R., Agema, A., Donker, G. H., Schwarz, F., and Thijssen, J. H. H. (1980). Adrenal androgen secretion and metabolism in postmenopausal women. In *Adrenal Androgens* (A. R. Genazzani, J. H. H. Thijssen and P. K. Siiteri eds.), pp. 219–240, Raven Press, New York.
15. Bird, C. E., Murphy, J., Boroomand, K., Finnis, W., Dressel, D., and Clark, A. F. (1978). Dehydroepiandrosterone: Kinetics of metabolism in normal men and women. *J. Clin. Endocrinol. Metab.* 47, 818–822.
16. Reed, M. J., Noel, C. T., Jones, D. L., Jacobs, H. S., Scanlon, M. J., and James, V. H. T. (1986). The use of nonradiolabelled steroid infusions to investigate the origin of oestrone sulphate in postmenopausal women. *Horm. Metabol. Res.* 18, 779–783.
17. Daynes, R. A., Araneo, B. A., Ershler, W. B., Maloney, C., Li, G., and Ryn, S. (1993). Altered regulation of IL-6 production with normal ageing. *J. Immunology,* 150, 5219–5230.
18. Rook, G. A. W., Hernandez-Pando, R., and Lightman, S. (1994). Hormones, peripherally activated prohormones and regulation of the TH1/TH2 balance. *Immunol. Today,* 15, 301–303.
19. Foulkes, R., Shaw, S., and Suitters, A. (1997). Immunological consequences of inhibiting dehydroepiandrosterone sulfatase in vivo. In *Steroid hormones and the T-cell cytokine profile* (G. A. W. Rook and S. Lightman eds.), pp. 135–152, Springer, Berlin.
20. Li, P. K., Rhodes, M. E., Jagannathan, S., and Johnson, D. A. (1995). Reversal of scopolamine induced amnesia in rats by the steroid sulfatase inhibitor estrone-3-O-sulfamate. *Cognit. Brain Res.* 2, 251–254.
21. Rhodes, M. E., Li, P. K., Burke, A. M., and Johnson, D. A. (1997). Enhanced plasma DHEAS, brain acetylcholine and memory mediated by steroid sulfatase inhibition. *Brain Research,* 773, 28–32.
22. Li, P. K., Rhodes, M. E., Burke, A. M., and Johnson, D. A. (1996). Memory enhancement mediated by the steroid sulfatase inhibitor (p-O-sulfamoyl)-N-tetradecanoyl tyramine. *Life Sciences,* 60, PL45–PL51.
23. Purohit, A., Dauvois, S., Parker, M. G., Potter, B. V. L., Williams, G. J., and Reed, M. J. (1994). The hydrolysis of oestrone sulphate and dehydroepiandrosterone sulphate by human steroid sulphatase expressed in transfected COS-1 cells. *J. Steroid Biochem. Molec. Biol.* 50, 101–104.
24. Howarth, N. M., Purohit, A., Reed, M. J., and Potter, B. V. L. (1994). Estrone sulfamates: potent inhibitors of estrone sulfatase with therapeutic potential. *J. Med. Chem.* 37, 219–221.
25. Purohit, A., Williams, G. J., Howarth, N. M., Potter, B. V. L., and Reed, M. J. (1995). Inactivation of steroid sulfatase by an active site-directed inhibitor, estrone-3-O-sulfamate. *Biochemistry,* 34, 11508–11514.
26. Purohit, A., Williams, G. J., Roberts, C. J., Potter, B. V. L., and Reed, M. J. (1995). In vivo inhibition of oestrone sulphatase and dehydroepiandrosterone sulphatase by oestrone-3-O-sulphamate. *Int. J. Cancer,* 63, 106–111.
27. U.S. Pat. No. 5,616,574 (1997).
28. Woo, L. W. L., Howarth, N. M., Purohit, A., Hejaz, H. A. M., Reed, M. J., and Potter, B. V. L. (1998). Steroidal and nonsteroidal sulfamates as potent inhibitors of steroid sulfatase. *J. Med. Chem.* 41, 1068–1083.
29. Elger, W., Schwarz, S., Hedden, A., Reddersen, G., and Schneider, B. (1995). Sulfamates of various estrogens—prodrugs with increased systemic and reduced hepatic estrogenicity at oral application. *J. Steroid Biochem. Molec. Biol.* 55, 395–403.
30. Woo, L. W. L., Purohit, A., Reed, M. J., and Potter, B. V. L. (1996). Active site-directed inhibition of estrone sulfatase by nonsteroidal coumarin sulfamates. *J. Med. Chem.* 39, 1349–1351.
31. Purohit, A., Woo, L. W. L., Singh, A., Winterborn, C. J., Potter, B. V. L., and Reed, M. J. (1996). In vivo activity of 4-methylcoumarin-7-O-sulfamate, a nonsteroidal, non-estrogenic steroid sulfatase inhibitor. *Cancer Res.* 56, 4950–4955.
32. Anderson, C., Freeman, J., Lucas, L. H., Farley, M., Dalhoumi, H., and Widlanski, T. S. (1997). Estrone sulfatase: Probing structural requirements for substrate and inhibitor recognition. *Biochemistry,* 36, 2586–2594.
33. Selcer, K. W., Hegde, P. V., and Li, P. K. (1997). Inhibition of estrone sulfatase and proliferation of human breast cancer cells by nonsteroidal (p-O-sulfamoyl)-N-alkanoyltyramines. *Cancer Res.* 57, 702–707.
34. Li, P. K., Milano, S., Kluth, L., and Rhodes, M. E. (1996). Synthesis and sulfatase inhibitory activities of non-steroidal estrone sulfatase inhibitors. *J. Steroid Biochem. Molec. Biol.* 59, 41–48.
35. Li, P. K., Chu, G., Guo, J., Peters, A., and Selcer, K. W. (1998). Development of potent non-estrogenic estrone sulfatase inhibitors. *Steroids,* 63, 425–432.
36. Ciobanu, L. C., Boivin, R. P., Luu-The, V., Labrie, F., and Poirier, D. (1999). Potent inhibition of steroid sulfatase activity by 3-O-sulfamate 17α-benzyl(or 4'-tert-butylbenzyl)estra-1,3,5(10)-trienes: combination of two substituents at positions C3 and C17α of estradiol. *J. Med. Chem.* 42, 2280–2286.
37. Woo, L. W. L., Lightowler, M., Purohit, A., Reed, M. J., and Potter, B. V. L. (1996). Heteroatom-substituted analogues of the active site-directed inhibitor estra-1,3,5(10)-trien-17-one-3-sulphamate inhibit estrone sulphatase by a different mechanism. *J. Steroid Biochem. Molec. Biol.* 57, 79–88.
38. Williams, G. J., Woo, L. W. L., Mahon, M. F., Purohit, A., Reed, M. J., and Potter, B. V. L. (1996). X-ray crystal structure and mechanism of action of oestrone 3-O-sulphamate, a synthetic active site-directed inhibitor of oestrone sulphatase. *Pharm. Sci.* 2, 11–16.
39. Anderson, C. J., Lucas, L. J. H., and Widlanski, T. S. (1995). Molecular recognition in biological systems: phosphate esters vs sulfate esters and the mechanism of action of steroid sulfatases. *J. Am. Chem. Soc.* 117, 3889–3890.
40. Bond, C. S., Clements, P. R., Ashby, S. J., Collyer, C. A., Harrop, S. J., Hopwood, J. J., and Guss, J. M. (1997). Structure of a human lysosomal sulfatase. *Structure,* 5, 277–289.
41. Recksiek, M., Selmer, T., Dierks, T., Schmidt, B., and von Figura, K. (1998). Sulfatases, trapping of the sulfated enzyme intermediate by substituting the active site formylglycine. *J. Biol. Chem.* 273, 6096–6103.
42. Lukatela, G., Krauss, N., Theis, K., Selmer, T., Gieselmann, V., von Figura, K., and Saenger, W. (1998). Crystal structure of human arylsulfatase A: the aldehyde function and the metal ion at the active site suggest a novel mechanism for sulfate ester hydrolysis. *Biochemistry,* 37, 3654–3664.
43. Waldow, A., Schmidt, B., Dierks, T., von Bülow, R., and von Figura, K. (1999). Amino acid residues forming the active site of arylsulfatase A: role in catalytic activity and substrate binding. *J. Biol. Chem.* 274, 12284–12288.

44. Bickoff, E. M., Booth, A. N., Lyman, R. L., Livingston, A. L., Thompson, C. R., and Kohler, G. O. (1958). Isolation of a new estrogen from Ladino clover. *J. Agr. Food Chem.* 6, 536–539.
45. Bickoff, E. M., Lyman, R. L., Livingston, A. L., and Booth, A. N. (1958). Characterization of coumestrol, a naturally occurring plant estrogen. *J. Am. Chem. Soc.* 80, 3969–3971.
46. Hua, D. H., Saha, S., Roche, D., Maeng, J. C., Iguchi, S., and Baldwin, C. (1992). An improved procedure of the Pechmann condensation in the synthesis of 8-ethyltrimethoxy-6H-benzo[d]naphtho[1,2-b]-pyran-6-ones structurally related to the Aglycon of Gilvocarcins. *J. Org. Chem.* 57, 399–403.
47. Prelog, V. and Kobelt, M. Carbon rings. L. (1949). The dependence of the dissociation constants of the ring-homologous cyclanone cyanohydrins upon the size of the ring. *Helv. Chim. Acta,* 32, 1187–1192.
48. Brown, H. C. and Ichikawa, K. (1957). Chemical effects of steric strains—XIV. The effect of ring size on the rate of reaction of the cyclanones with sodium borohydride. *Tetrahedron,* 1, 221–230.
49. Kitz, R. and Wilson, I. B. (1962). Esters of methanesulfonic acid as irreversible inhibitors of acetylcholinesterase. *J. Biol. Chem.* 237, 3245–3249.
50. Ermolaeva, L. I., Mastryukov, V. S., Allinger, N. L., and Almenningen, A. (1989). Molecular-structure of cycloheptene, $C_7H_{12}$, as determined by electron-diffraction and molecular mechanics. *J. Mol. Struct.* 196, 151–156.
51. Purohit, A., Vernon, K. A., Wagenaar Hummelinck, A. E., Woo, L. W. L., Hejaz, H. A. M., Potter, B. V. L., and Reed, M. J. (1998). The development of A-ring modified analogues of oestrone-3-O-sulphamate as potent steroid sulphatase inhibitors with reduced oestrogenicity. *J. Steroid Biochem. Molec. Biol.* 64, 269–275.
52. Schmidt, B., Selmer, T., Ingendoh, A., and von Figura, K. (1995). A Novel Amino Acid Modification in Sulfatases That Is Defective in Multiple Sulfatase Deficiency. *Cell,* 82, 271–278.
53. Knaust, A., Schmidt, B., Dierks, T., von Bülow, R., and von Figura, K. (1998). Residues critical for formylglycine formation and/or catalytic activity of arylsulfatase A. *Biochemistry,* 37, 13941–13946.
54. Franco, B., Meroni, G., Parenti, G., Levilliers, J., Bernard, L., Gebbia, M., Cox, L., Maroteaux, P., Sheffield, L., Rappold, G. A., Andria, G., Petit, C., and Ballabio, A. (1995). A cluster of sulfatase genes on Xp22.3: mutations in chondrodysplasia punctata (CDPX) and implications for warfarin embryopathy. *Cell,* 81, 15–25.
55. Dierks, T., Schmidt, B., and von Figura, K. (1997). Conversion of cysteine to formylglycine: a protein modification in the endoplasmic reticulum. *Proc. Natl. Acad. Sci. USA,* 94, 11963–11968.
56. Selmer, T., Hallmann, A., Schmidt, B., Sumper, M., and von Figura, K. (1996). The evolutionary conservation of a novel protein modification, the conversion of cysteine to serinesemialdehyde in arylsulfatase from *Volvox carteri*. *Eur. J. Biochem.* 238, 341–345.
57. Thea, S., Cevasco, G., Guanti, G., and Williams, A. (1986). The anionic sulphonylamine mechanism in the hydrolysis of aryl sulphamates. *J. Chem. Soc. Chem. Commun.,* 1582–1583.
58. Sahm, U. G., Williams, G. J., Purohit, A., Hidalgo aragones, M. I., Parish, D., Reed, M. J., Potter, B. V. L., and Pouton, C. W. (1996). Development of an oral formulation for oestrone 3-O-sulphamate, a potent sulphatase inhibitor. *Pharm. Sci.* 2, 17–20.
59. Williams, A. and Douglas, K. T. (1974). Hydrolysis of aryl N-methylaminosulphonates: evidence consistent with an E1cB mechanism. *J. Chem. Soc. Perkin Trans.* 2, 1727–1732.
60. Spillane, W. J., Hogan, G., and McGrath, P. (1995). Aminolysis and hydrolysis of sulphamate esters: substantial N=S bonding in the transition state leading to N=sulfonylamines. *J. Phys. Org. Chem.,* 8, 610–616.
61. Albert, A. and Serjeant, E. P. (1984). *The determination of ionization constants*. Chapman and Hall, New York.
62. Fersht, A. (1984). The pH dependence of enzyme catalysis. In *Enzyme structure and mechanism*. Ch. 5. p. 155, W.H. Freeman and company, New York.
63. Spillane, W. J., Hogan, G., McGrath, P., King, J., and Brack, C. (1996). Aminolysis of sulfamate esters in non-aqueous solvents. Evidence consistent with a concerted E2-type mechanism. *J. Chem. Soc. Perkin Trans.* 2, 2099–2104.
64. Spillane, W. J., Hogan, G., McGrath, P., and King, J. (1998). Aminolysis of sulfamate esters in chloroform—nonlinear kinetics. *J. Chem. Soc. Perkin Trans.* 2, 309–313.
65. Spillane, W. J., McGrath, P., Brack, C., and Barry, K. (1998). Novel change in rate-determining step within an E1cB mechanism during aminolysis of a sulfamate ester in acetonitrile. *Chem. Commun.* 1017–1018.
66. Appel, R. and Berger, G. (1958) Über das Hydrazidosulfamid. (On hydrazidosulfamide.). *Chem. Ber.* 91, 1339–1341.
67. Duncan, L., Purohit, A., Howarth, N. M., Potter, B. V. L., and Reed, M. J. (1993). Inhibition of estrone sulfatase activity by estrone-3-methylthiophosphonate: a potential therapeutic agent in breast cancer. *Cancer Res.* 53, 298–303.
68. Mentzer, C., Gley, P., Molho, D., and Billet, D. (1946). Estrogenic substances of the coumarin series. II. *Bull. Soc. Chim. Fr.* 271–276.
69. Kotwani, N. G., Sethna, S. M., and Advani, G. D. (1942). Pechmann condensation of phenols with ethyl butyrylacetate. *Proc. Indian Acad. Sci.* 15A, 441–444.
70. John, E. V. O. and Israelstam, S. S. (1961). Use of cation exchange resins in organic reactions. I. The von Pechmann reaction. *J. Org. Chem.* 26, 240–242.
71. Barbry, D., Faven, C., and Ajana, A. (1994). Improved alkylation of ethyl acetoacetate and diethyl malonate. *Bioorg. Med. Chem. Lett.* 7, 3075–3080.
72. Yoffe, S. T., Vatsuro, K. V., Kugutcheva, E. E., and Kabachnik, M. I. (1965). Dual reactivity of sodium ethyl acetoacetate by alkylation with alkyl halides. *Tett. Lett.* 593–600.
73. Sethna, S. M. and Shah, R. C. (1938). Pechmann's condensation of methyl β-resorcylate with ethyl α-alkylacetoacetates. *J. Indian Chem. Soc.* 15: 383–388.
74. Pillon, D. (1952). Benzopyrones. New condensations of phenol with β-ketonic esters. *Bull. Soc. Chim. Fr.* 324–330.
75. Desai, R. D., Gaitonde, M. M., Hasan, S. M., and Shah, R. C. (1947). Heterocyclic compounds. XVIII. Condensation of cyclic β-ketonic esters with methyl β-resorcylate and resacetophenone in the presence of anhydrous aluminium chloride. *Proc. Indian Acad. Sci.* 25A, 345–350.
76. Palau, J., Pascual, J., and Rafols, J. M. (1964). cis- and trans-2-Hydroxycycloheptane-carboxylic acids. Comparison with their cyclopentane and cyclohexane analogs. *Bull. Soc. Chim. Fr.* 269–273.
77. Hua, D. H., Saha, S., Maeng, J. C., and Bensoussan, D. (1990). The Pechmann reaction and regioselective oxidation with selenium oxide. Synthesis of the 12-Demethoxydefuco-gilvocarin ring system. *Synlett*, 233–234.

The invention claimed is:

1. A method of treating an endocrine dependent tumour in a subject in needed thereof, comprising administering to said subject an effective amount of a non-steroidal compound of general Formula (B)

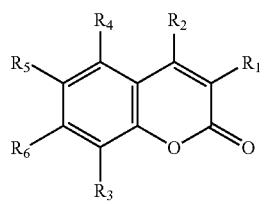

(B)

wherein $R_1$–$R_5$ are independently selected from H, halo, hydroxy, sulphamate, alkyl and substituted variants or salts thereof; wherein $R_6$ is a sulphamate group; and wherein $R_1$–$R_2$ are optionally linked together to form an additional cyclic structure having 3–14 carbon atoms.

2. The method of claim 1, wherein the compound is selected from the group consisting of compounds D, E, F, G and H wherein $R_3$ to $R_5$ are independently selected from H, halo, hyroxy, sulphamate, alkyl and substituted variants or salts thereof, wherein $R_6$ is a sulphamate group.

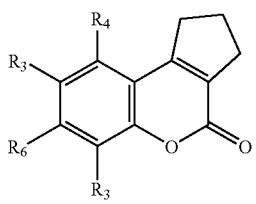

D

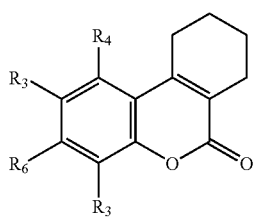

E

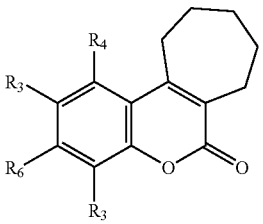

F

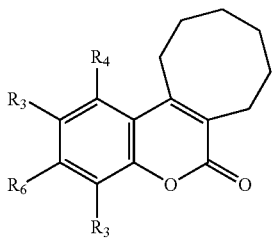

G

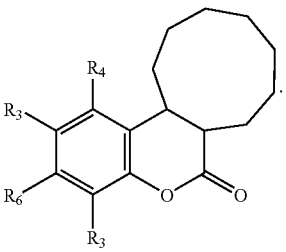

H

3. The method of claim 2, wherein the compound is F.

4. The method of claim 1, wherein $R_1$–$R_5$ are independently selected from H, alkyl and haloalkyl; preferably wherein $R_1$–$R_5$ are independently selected from H, $C_{1-6}$ alkyl and $C_{1-6}$ haloalkyl.

5. The method of claim 4, wherein $R_1$–$R_5$ are independently selected from H, $C_{1-3}$ alkyl and $C_{1-3}$ haloalkyl.

6. The method of claim 5, wherein $R_1$–$R_5$ are independently selected from H, methyl and halomethyl.

7. The method of claim 1, wherein $R_6$ is selected from $OSO_3$ and $OSO_2NH_2$.

8. A method of treating a breast cancer tumour in a subject in need thereof, comprising administering to said subject an effective amount of a non-steroidal compound of general Formula (B)

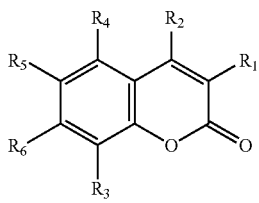

(B)

wherein $R_1$–$R_5$ are independently selected from H, halo, hydroxy, sulphamate, alkyl and substituted variants or salts thereof; wherein $R_6$ is a sulphamate group; and wherein $R_1$–$R_2$ are optionally linked together to form an additional cyclic structure having 3–14 carbon atoms.

* * * * *

UNITED STATES PATENT AND TRADEMARK OFFICE
CERTIFICATE OF CORRECTION

PATENT NO.         : 7,202,272 B2
APPLICATION NO.    : 10/991137
DATED              : April 10, 2007
INVENTOR(S)        : Michael John Reed and Barry Victor Lloyd Potter It is certified that error appears in the above-identified patent and that said Letters Patent is hereby corrected as shown below:

Column 41, Claim 1 line 6 should read

1. A method of treating an endocrine dependent tumour in a subject in

"needed" <u>need</u> thereof, comprising administering to said subject an effective amount of a non-steroidal compound of general Formula (B)

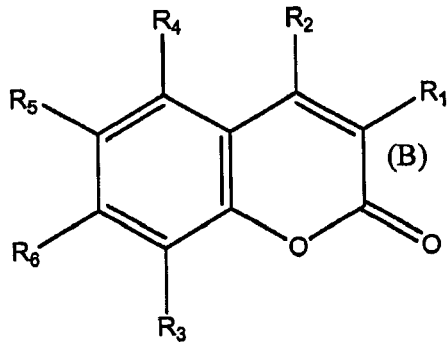

wherein $R_1$-$R_5$ are independently selected from H, halo, hydroxy, sulphamate, alkyl and substituted variants or salts thereof; wherein $R_6$ is a sulphamate group; and wherein $R_1$-$R_2$ are optionally linked together to form an additional cyclic structure having 3-14 carbon atoms.

UNITED STATES PATENT AND TRADEMARK OFFICE
CERTIFICATE OF CORRECTION

PATENT NO. : 7,202,272 B2
APPLICATION NO. : 10/991137
DATED : April 10, 2007
INVENTOR(S) : Michael John Reed and Barry Victor Lloyd Potter It is certified that error appears in the above-identified patent and that said Letters Patent is hereby corrected as shown below:

Column 41, Claim 2, line 30 should read

2. The method of claim 18, wherein the compound is selected from the group consisting of compounds D, E, F, G and H wherein $R_3$ to $R_5$ are independently selected from H, halo, "hyroxy" hydroxy, sulphamate, alkyl and substituted variants or salts thereof, wherein $R_6$ is a sulphamate group"."

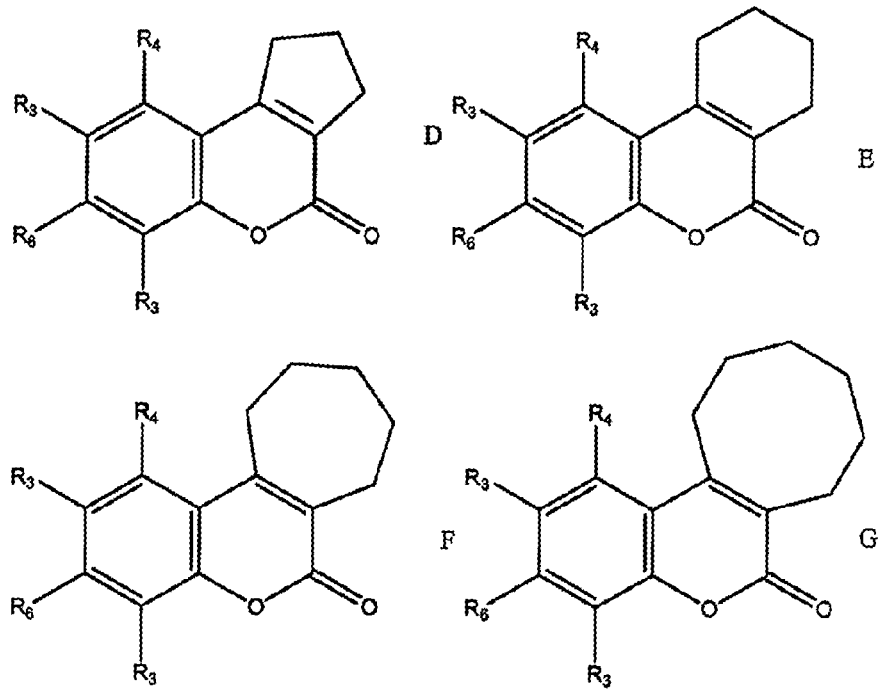

UNITED STATES PATENT AND TRADEMARK OFFICE
CERTIFICATE OF CORRECTION

PATENT NO.         : 7,202,272 B2
APPLICATION NO.    : 10/991137
DATED              : April 10, 2007
INVENTOR(S)        : Michael John Reed and Barry Victor Lloyd Potter It is certified that error appears in the above-identified patent and that said Letters Patent is hereby corrected as shown below:

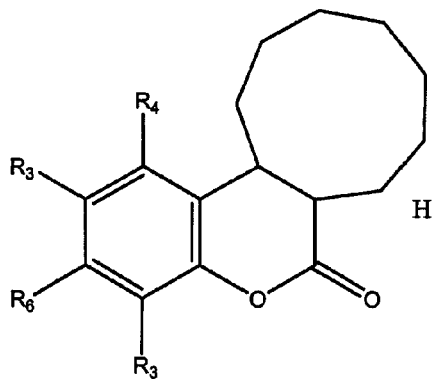

Signed and Sealed this

Second Day of September, 2008

JON W. DUDAS
*Director of the United States Patent and Trademark Office*